(12) United States Patent
Calabria et al.

(10) Patent No.: US 8,129,413 B2
(45) Date of Patent: Mar. 6, 2012

(54) CRYSTALLINE FORMS OF MC4R AGONIST AND PROCESS FOR SYNTHESIS

(75) Inventors: Ralph Calabria, East Brunswick, NJ (US); Yu Cheng, Harleysville, PA (US); Russell R. Ferlita, Westfield, NJ (US); Ashkan Kamali, West Conshohocken, PA (US); Jerry A. Murry, Jersey City, NJ (US); David Mathre, Skillman, NJ (US); Andrey V. Peresypkin, Cranford, NJ (US); Karen Thompson, Lansdale, PA (US); Jian Wang, Neshanic Station, NJ (US); Robert M. Wenslow, Cream Ridge, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 1027 days.

(21) Appl. No.: 11/921,824

(22) PCT Filed: Jun. 23, 2006

(86) PCT No.: PCT/US2006/024573
§ 371 (c)(1),
(2), (4) Date: Dec. 7, 2007

(87) PCT Pub. No.: WO2007/002462
PCT Pub. Date: Jan. 4, 2007

(65) Prior Publication Data
US 2009/0233967 A1     Sep. 17, 2009

Related U.S. Application Data

(60) Provisional application No. 60/694,488, filed on Jun. 27, 2005.

(51) Int. Cl.
*A61K 31/454* (2006.01)
*C07D 401/06* (2006.01)
(52) U.S. Cl. ........................................ 514/326; 546/208
(58) Field of Classification Search .................. 514/326; 546/208
See application file for complete search history.

(56) References Cited

U.S. PATENT DOCUMENTS

| 5,741,819 A | 4/1998 | Illig et al. |
| 6,818,658 B2 | 11/2004 | Ujjainwalla et al. |
| 2003/0225060 A1 | 12/2003 | Ujjainwalla et al. |

FOREIGN PATENT DOCUMENTS

| WO | WO 02/068388 | 9/2002 |

OTHER PUBLICATIONS

Seddon "Pseudopolymorph . . . " Crystal growth & design p. 1087 (2004) (two pares form internet).*
Braga et al. :Making crystals . . . J. royal Soc. chem. Chem. Commun. p. 3635-3645 (2005).*

(Continued)

*Primary Examiner* — Celia Chang
(74) *Attorney, Agent, or Firm* — Kenrick L. Vidale; John C. Todaro

(57) ABSTRACT

The present invention relates to a process for producing N-{(1S)-1-[2-(1-{[(3S,4R)-1-tert-butyl-4-(2,4-difluorophenyl)pyrrolidin-3-yl]carbonyl}piperidin-4-yl)-5-chlorophenyl]ethyl}acetamide, and novel crystalline salts, hydrates, solvates, and polymorphic forms thereof.

11 Claims, 9 Drawing Sheets

OTHER PUBLICATIONS

Exhibit I (2011).*
Peresypsin et al. "discovery of a . . . " J. Pharm. Science v. 97(9) p. 3721-3726 (2008).*
Kirk-Othmer "Crystallization" Encyclopedia of chemi. Tech. vol. 8, p. 95-147 (2002).*
Davidovich et al. "Detection of polymorphism . . . " Am. Pharm. Rev. vo. 7(1) p. 10, 12, 14, 16, 100 (2004).*
H. G. Brittain, "Polymorphism in Pharmaceutical Solids", Marcel Dekker (1999).

* cited by examiner

CRYSTALLINE FORMS OF MC4R AGONIST AND PROCESS FOR SYNTHESIS

CROSS-REFERENCE TO RELATED APPLICATIONS

This application is a U.S. National Phase application under 35 U.S.C. §371 of PCT Application No. PCT/US2006/024573, filed Jun. 23, 2006, which claims priority under 35 U.S.C. §119 from U.S. provisional application No. 60/694,488, filed Jun. 27, 2005.

BACKGROUND OF THE INVENTION

The present invention provides a process for the preparation of N-{(1S)-1-[2-(1-{[(3S,4R)-1-tert-butyl-4-(2,4-difluorophenyl)pyrrolidin-3-yl]carbonyl}piperidin-4-yl)-5-chlorophenyl]ethyl}acetamide (Compound I)

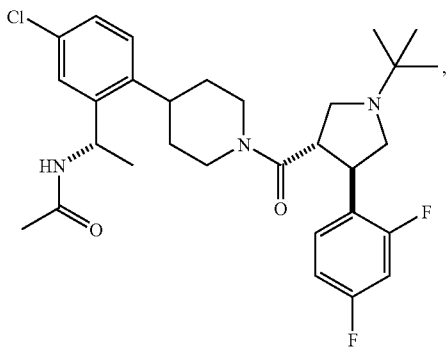

and crystalline salts, hydrates and polymorphs thereof.

Compound I is a selective melanocortin 4 receptor agonist useful for the treatment, control, or prevention of disorders responsive to the activation of MC-4R, such as obesity, obesity-related disorders, diabetes, metabolic syndrome, male sexual dysfunction, including erectile dysfunction, and female sexual dysfunction.

International Patent Application No. WO 02/068388 and US Patent Publication No. 2003/0225060 disclose Compound I and a process for its preparation. While the crystal forms produced in WO 02/068388 and US Patent Publication No. 2003/0225060 are not specifically addressed, the disclosed processes for the preparation of Compound I in these applications yield Compound I as an amorphous free base and as an amorphous mono hydrochloride salt. Neither the free base nor the amorphous salt is ideal for pharmaceutical formulation. The free base is unstable, photosensitive and thermally sensitive, and subject to oxidation if stored at a temperature greater than −40° C. The amorphous mono hydrochloride salt, formed by lyophilization or spray drying, is difficult to purify and has poor flow properties. It is therefore desirable to obtain crystalline forms of Compound I with improved physical and chemical stability, and fewer impurities for the preparation of a solid pharmaceutical dosage forms containing Compound I as the active pharmaceutical ingredient.

SUMMARY OF THE INVENTION

The present invention provides for crystalline salts, hydrates and polymorphs of N-{(1S)-1-[2-(1-{[(3S,4R)-1-tert-butyl-4-(2,4-difluorophenyl)pyrrolidin-3-yl]carbonyl}piperidin-4-yl)-5-chlorophenyl]ethyl}acetamide (Compound I).

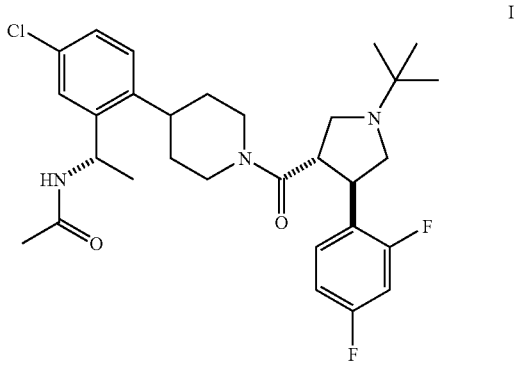

The present invention further provides for a process for the preparation of N-{(1S)-1-[2-(1-{[(3S,4R)-1-tert-butyl-4-(2,4-difluorophenyl) pyrrolidin-3-yl]carbonyl}piperidin-4-yl)-5-chlorophenyl]ethyl}acetamide (Compound I), and crystalline salts, hydrates and polymorphs thereof.

The following eight crystalline forms of salts Compound (I) that have been identified: 1) the crystalline hydrate mono HCl salt; 2) the crystalline anhydrous mono HCl salt Form I; 3) the crystalline anhydrous mono HCl salt Form II; 4) the crystalline bis HCl salt Form I; 5) the crystalline bis HCl salt Form II; 6) the hemi-hydrate bis HCl salt; 7) the crystalline bis HCl salt isopropanol/isopropyl acetate co-solvate; and 8) the crystalline mono HBr salt. Additionally, crystalline perchlorate, tetrafluoroborate, hexafluoroantimonate, and hexafluorophosphate salts of Compound I have also been isolated. Furthermore, three crystalline co-solvates of the free base of Compound I have been identified: 1) methanol/water co-solvate; 2) the ethanol/water co-solvate; and 3) the isopropanol/water co-solvate; each of these crystalline co-solvates exists in a 1:1:1 ratio of Compound I to solvent to water. The above crystalline salts, hydrates, hemi-hydrates and solvates of Compound I are new and have improved physiochemical properties, such as purity, stability and ease of formulation that render them particularly suitable for the manufacture of pharmaceutical dosage forms.

The anhydrous mono hydrochloric acid salt and anhydrous bis hydrochloric acid salt of Compound I have been found to exist in the following polymorphic forms: mono HCl hydrate, mono HCl salt Form I, mono HCl salt Form II, bis HCl salt Form I and bis HCl salt Form II, each of which can be formed by careful control of the crystallization conditions. At ambient conditions, the most thermodynamically stable crystalline form of Compound I is the crystalline hydrate mono hydrochloride salt. The most thermodynamically stable crystalline form at room temperature is important in that it provides bulk material with crystal homogeneity that is not subject to transforming to another crystal form on storage.

The present invention also relates to pharmaceutical formulations comprising the novel salts, hydrates and polymorphs of Compound I as active pharmaceutical ingredients, as well as methods for using them as melanocortin 4-receptor agonists in the treatment of melanocortin 4 receptor related disorders.

DETAILED DESCRIPTION OF THE INVENTION

The present invention is directed to salts, hydrates, solvates and polymorphic forms of N-{(1S)-1-[2-(1-{[(3S,4R)-1-tert-butyl-4-(2,4-difluorophenyl) pyrrolidin-3-yl]carbonyl}piperidin-4-yl)-5-chlorophenyl]ethyl}acetamide (Compound I).

The present invention further provides for a process for the preparation of Compound I from N-[(1S)-1-(5-chloro-2-piperidin-4-ylphenyl)ethyl]acetamide (II) or a salt thereof, and (3S,4R)-1-tert-butyl-4-(2,4-difluorophenyl) pyrrolidine-3-carboxylic acid (III) or a salt thereof, in the presence of a coupling agent (see Scheme A).

Scheme A

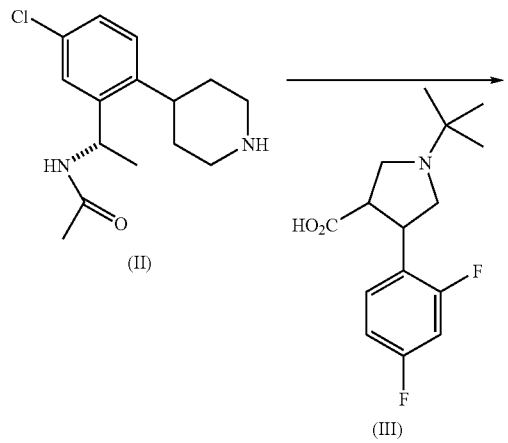

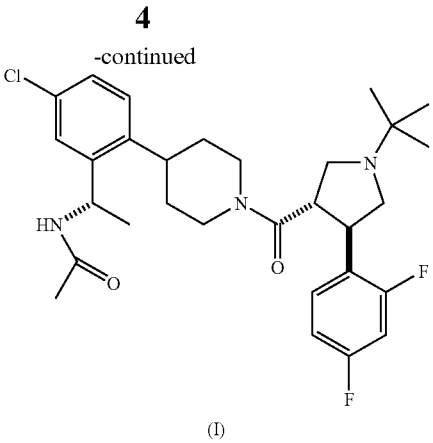

The terms "1N-{(1S)-1-[(2-(1-{[(3S,4R)-1-tert-butyl-4-(2,4-difluorophenyl) pyrrolidin-3-yl]carbonyl}piperidin-4-yl)-5-chlorophenyl]ethyl}acetamide" and "Compound I" comprise not only the free base forms of Compound I, but also any amorphous, partially crystalline or crystalline forms of Compound I, including glasses, lyophilates, and mixtures thereof, which may be converted to Compound I through warming. The present invention also comprehends all salts, hydrates, solvates and polymorphs of Compound I, and mixtures thereof.

The crystalline hydrochloride and hydrobromide salts of Compound I are characterized by the X-ray powder diffraction d-spacings given below and by the spectra in FIGS. 1 to 9.

Figure 1:
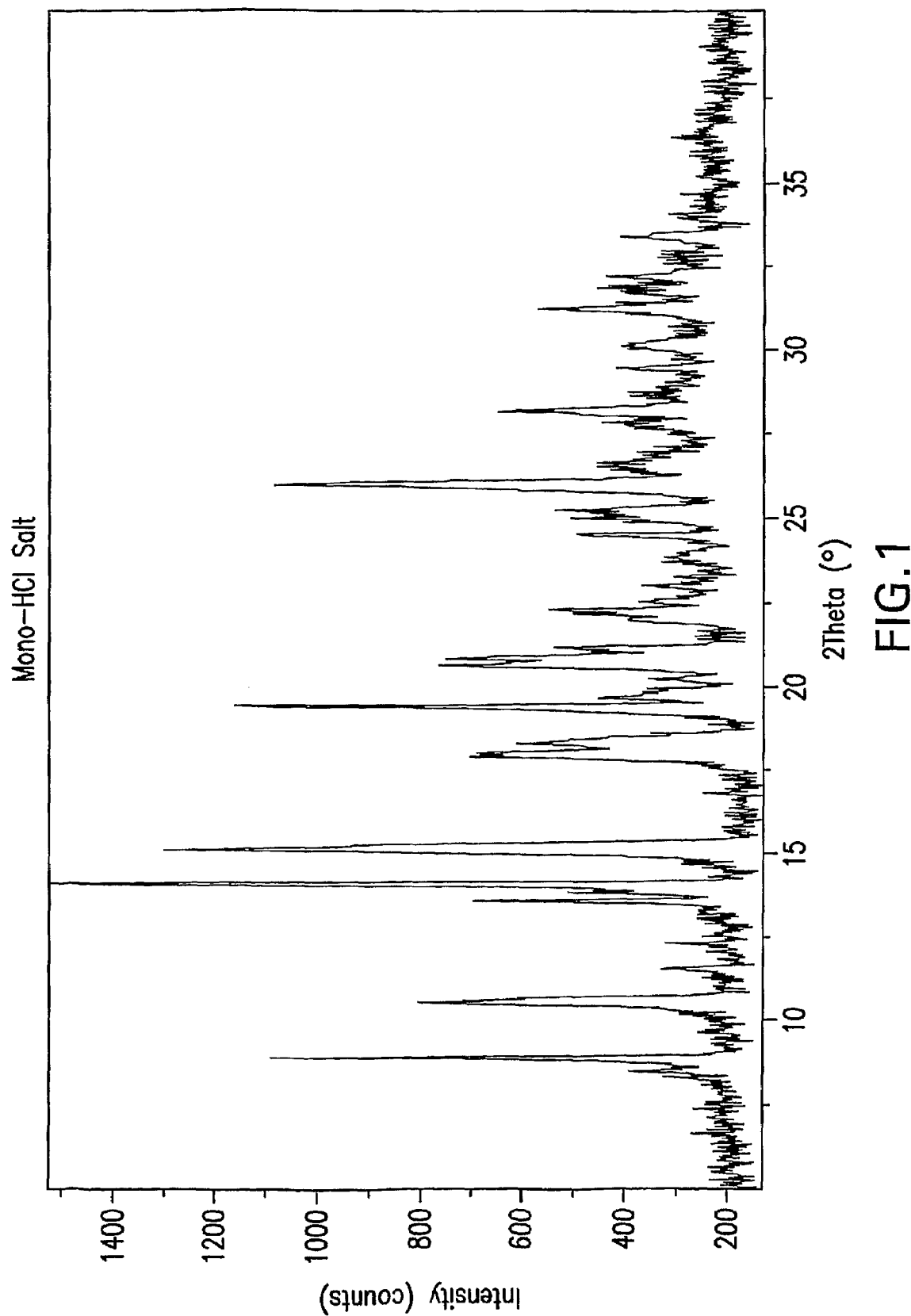
FIG. 1 is a characteristic X-ray diffraction pattern of the crystalline hydrate mono HCl salt of Compound I.

The crystalline hydrate mono HCl salt of N-{(1S)-1-[2-(1-{[(3S,4R)-1-tert-butyl-4-(2,4-difluorophenyl) pyrrolidin-3-yl]carbonyl}piperidin-4-yl)-5-chlorophenyl] ethyl}acetamide (Compound I) is characterized by diffraction peaks obtained from an X-ray powder diffraction pattern at spectral d-spacings of 6.3, 5.9, and 4.6 angstroms; is further characterized by the d-spacings of 10.0, 5.8, and 3.4 angstroms; and is even further characterized by the d-spacings of 8.4, 5.0, and 4.3 angstroms (see FIG. 1).

Figure 2:
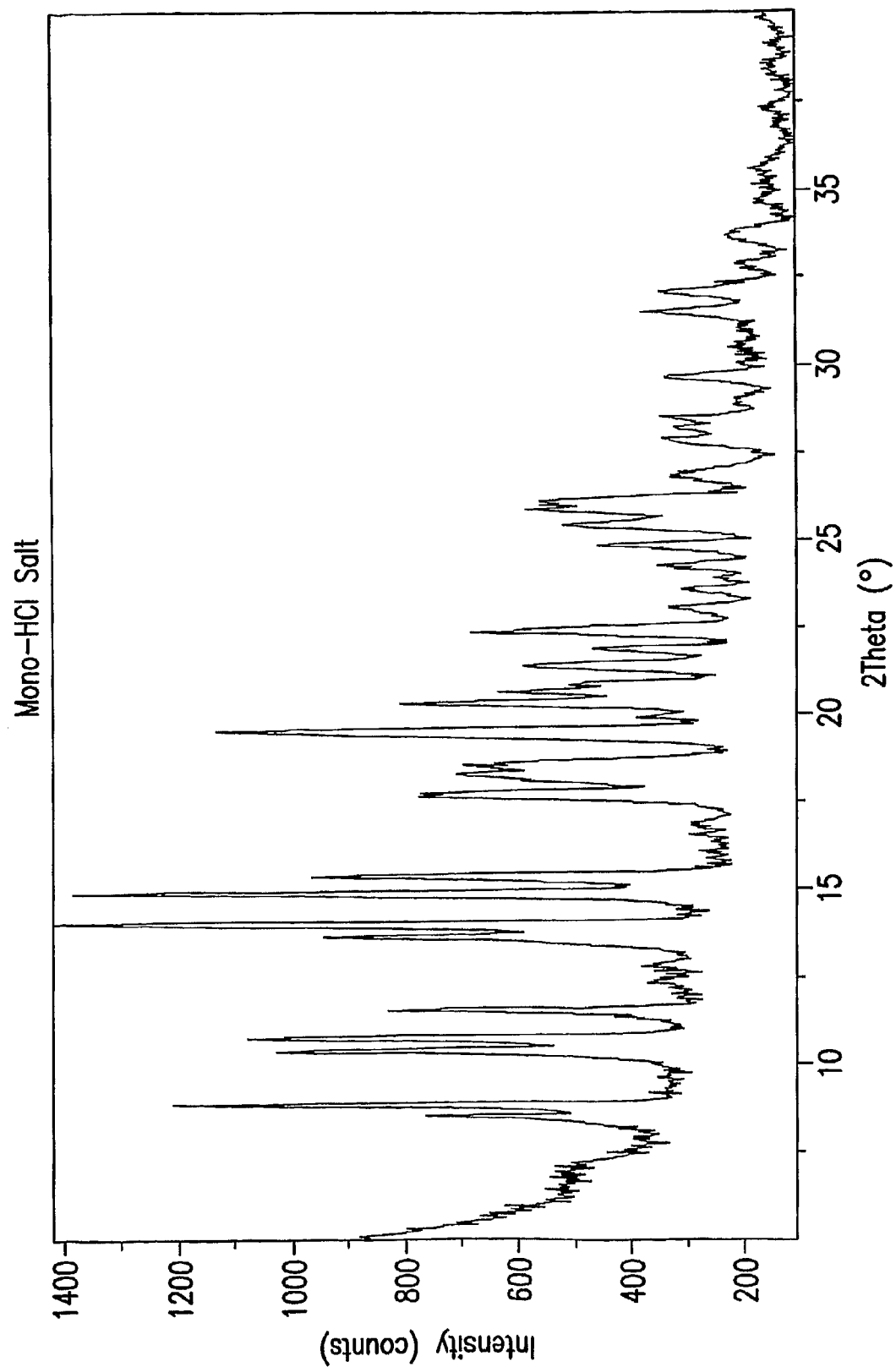
FIG. 2 is a characteristic X-ray diffraction pattern of the crystalline anhydrous mono HCl salt Form I of Compound I.

The crystalline anhydrous mono HCl salt Form I of N-{(1S)-1-[2-(1-{[(3S,4R)-1-tert-butyl-4-(2,4-difluorophenyl) pyrrolidin-3-yl]carbonyl}piperidin-4-yl)-5-chlorophenyl]ethyl}acetamide (Compound I) is characterized by diffraction peaks obtained from an X-ray powder diffraction pattern corresponding to spectral d-spacings of 6.3, 6.0, and 4.6 angstroms; is further characterized by the d-spacings of 10.0, 8.2, and 5.8 angstroms; and is even further characterized by the d-spacings of 8.5, 6.5, and 4.4 angstroms (see FIG. 2).

Figure 3:
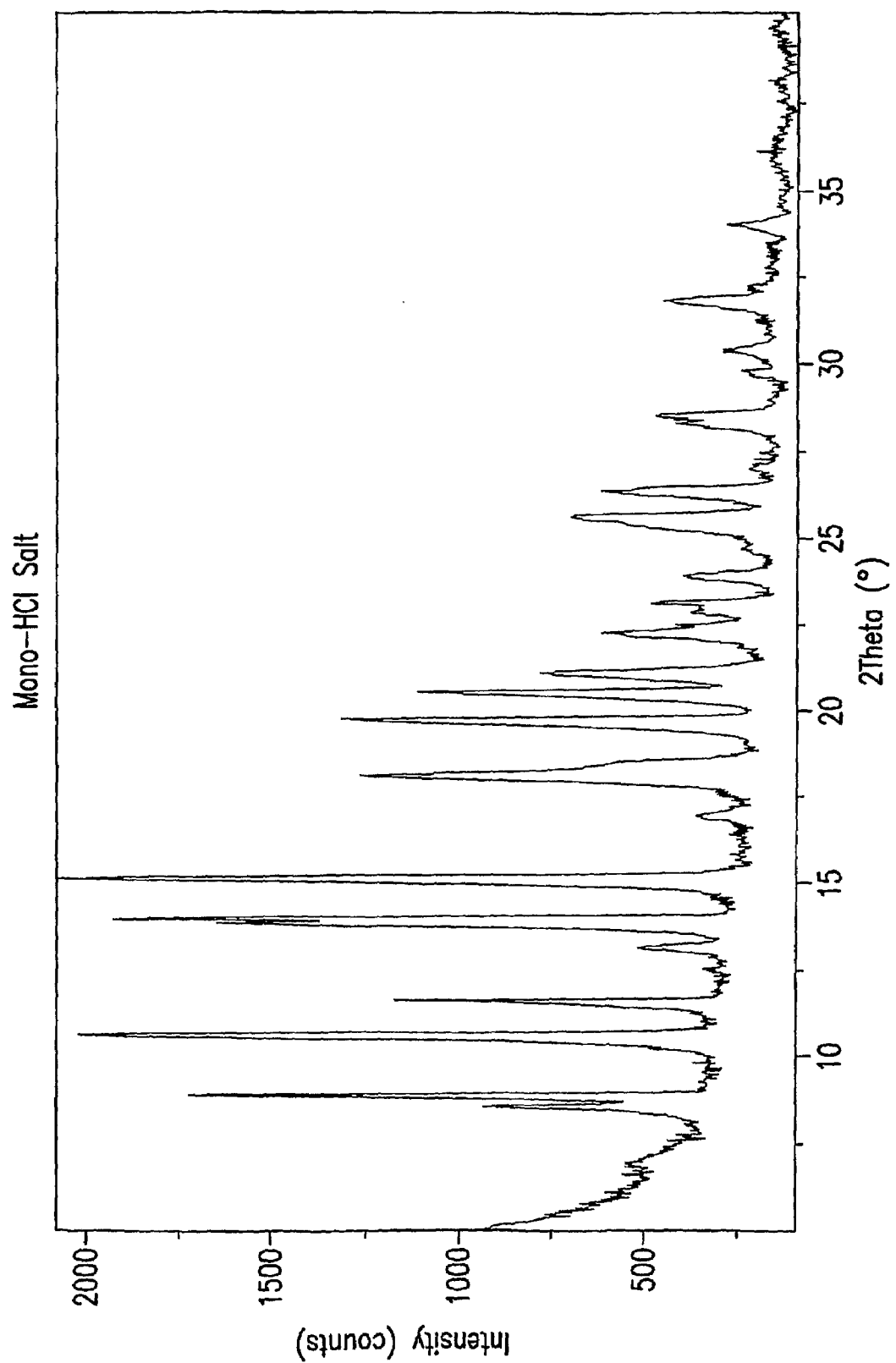
FIG. 3 is a characteristic X-ray diffraction pattern of the crystalline anhydrous mono HCl salt Form II of Compound I.

The crystalline anhydrous mono HCl salt Form II of N-{(1S)-1-[2-(1-{[(3S,4R)-1-tert-butyl-4-(2,4-difluorophenyl) pyrrolidin-3-yl]carbonyl}piperidin-4-yl)-5-chlorophenyl]ethyl}acetamide (Compound I) is characterized by diffraction peaks obtained from an X-ray powder diffraction pattern at spectral d-spacings of 8.3, 6.4, and 5.9 angstroms; is further characterized by the d-spacings of 9.9, 4.9 and 4.5 angstroms; and is even further characterized by the d-spacings of 7.6, 4.3, and 4.2 angstroms (see FIG. 3).

Figure 4:
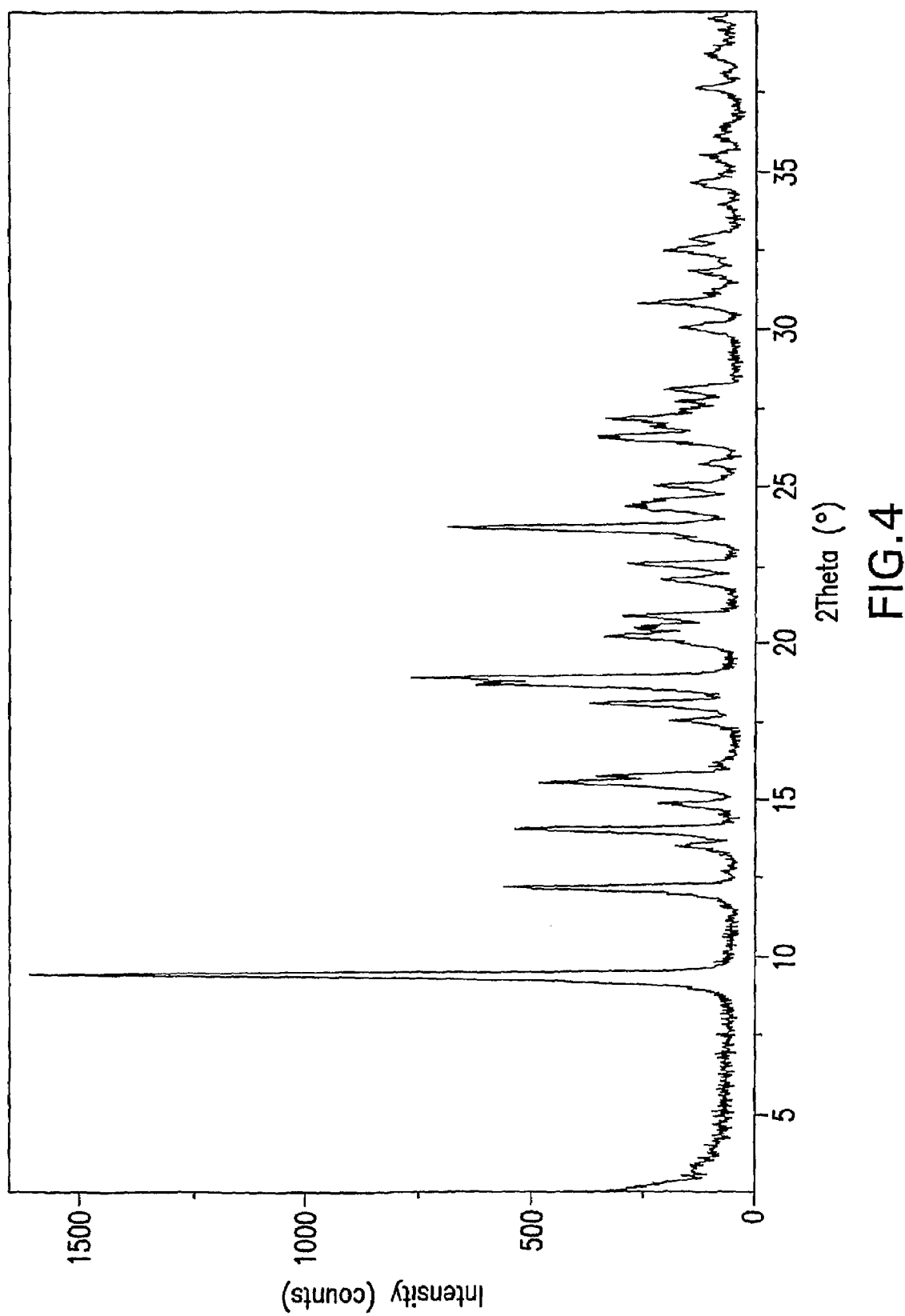
FIG. 4 is a characteristic X-ray diffraction pattern of the crystalline bis HCl salt Form I of Compound I.

The crystalline bis HCl salt Form I of N-{(1S)-1-[2-(1-{[(3S,4R)-1-tert-butyl-4-(2,4-difluorophenyl) pyrrolidin-3-yl]carbonyl}piperidin-4-yl)-5-chlorophenyl] ethyl}acetamide (Compound I) is characterized by diffraction peaks obtained from an X-ray powder diffraction pattern at spectral d-spacings of 9.4, 4.7, and 3.7 angstroms; is further characterized by the d-spacings of 7.2, 6.3, and 4.8 angstroms; and is further characterized by the d-spacings of 5.7, 3.4, and 3.3 angstroms (see FIG. 4).

Figure 5:
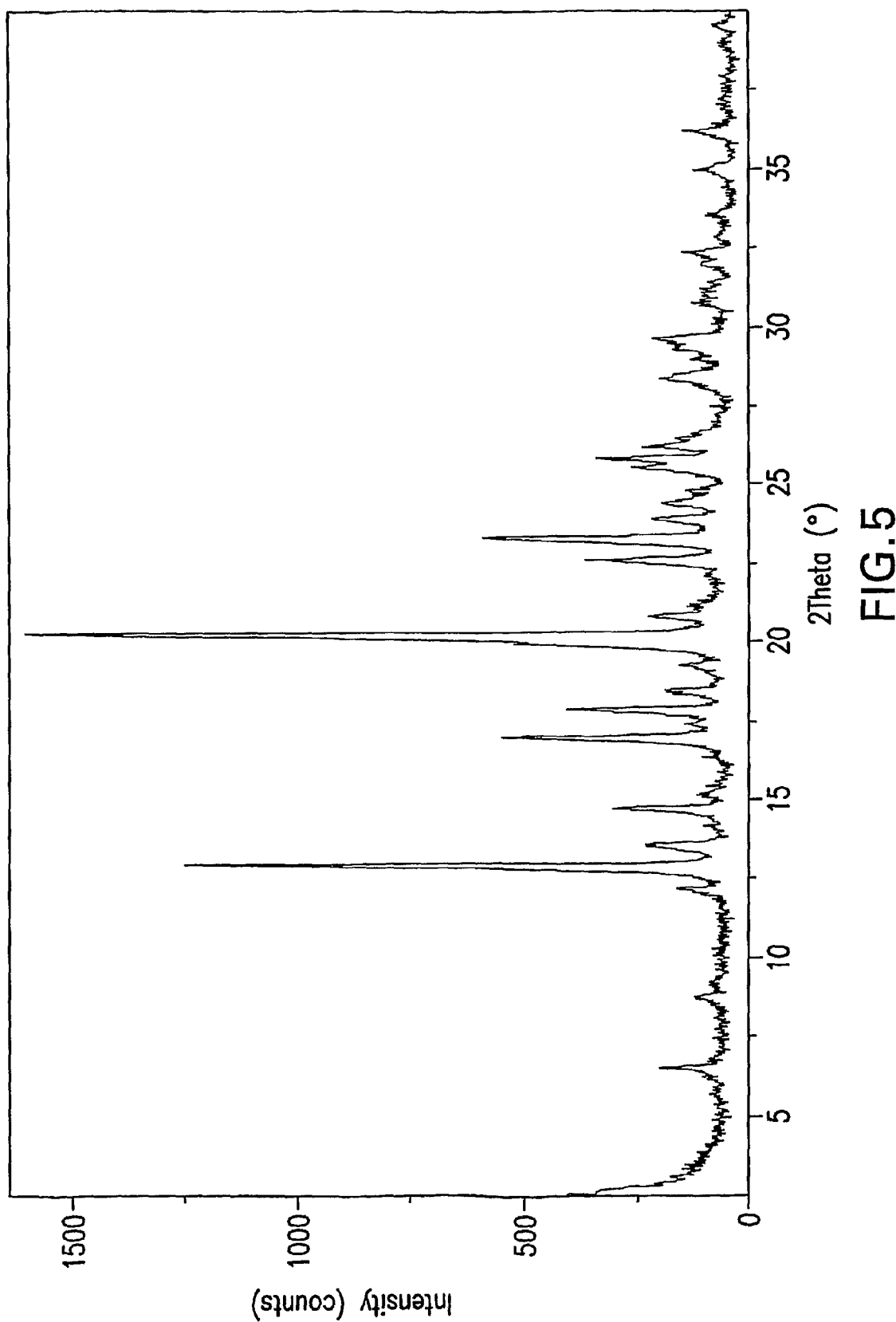
FIG. 5 is a characteristic X-ray diffraction pattern of the crystalline bis HCl salt Form II of Compound I.

The crystalline bis HCl salt Form II of N-{(1S)-1-[2-(1-{[(3S,4R)-1-tert-butyl-4-(2,4-difluorophenyl) pyrrolidin-3-yl]carbonyl}piperidin-4-yl)-5-chlorophenyl]ethyl}acetamide (Compound I) is characterized by characteristic diffraction peaks obtained from an X-ray powder diffraction pattern corresponding to spectral d-spacings of 6.9, 5.2, and 4.4 angstroms; is further characterized by the d-spacings of 5.0, 3.9 and 3.8 angstroms; and is even further characterized by the d-spacings of 6.0, 3.7, and 3.5 angstroms (see FIG. 5).

Figure 6:
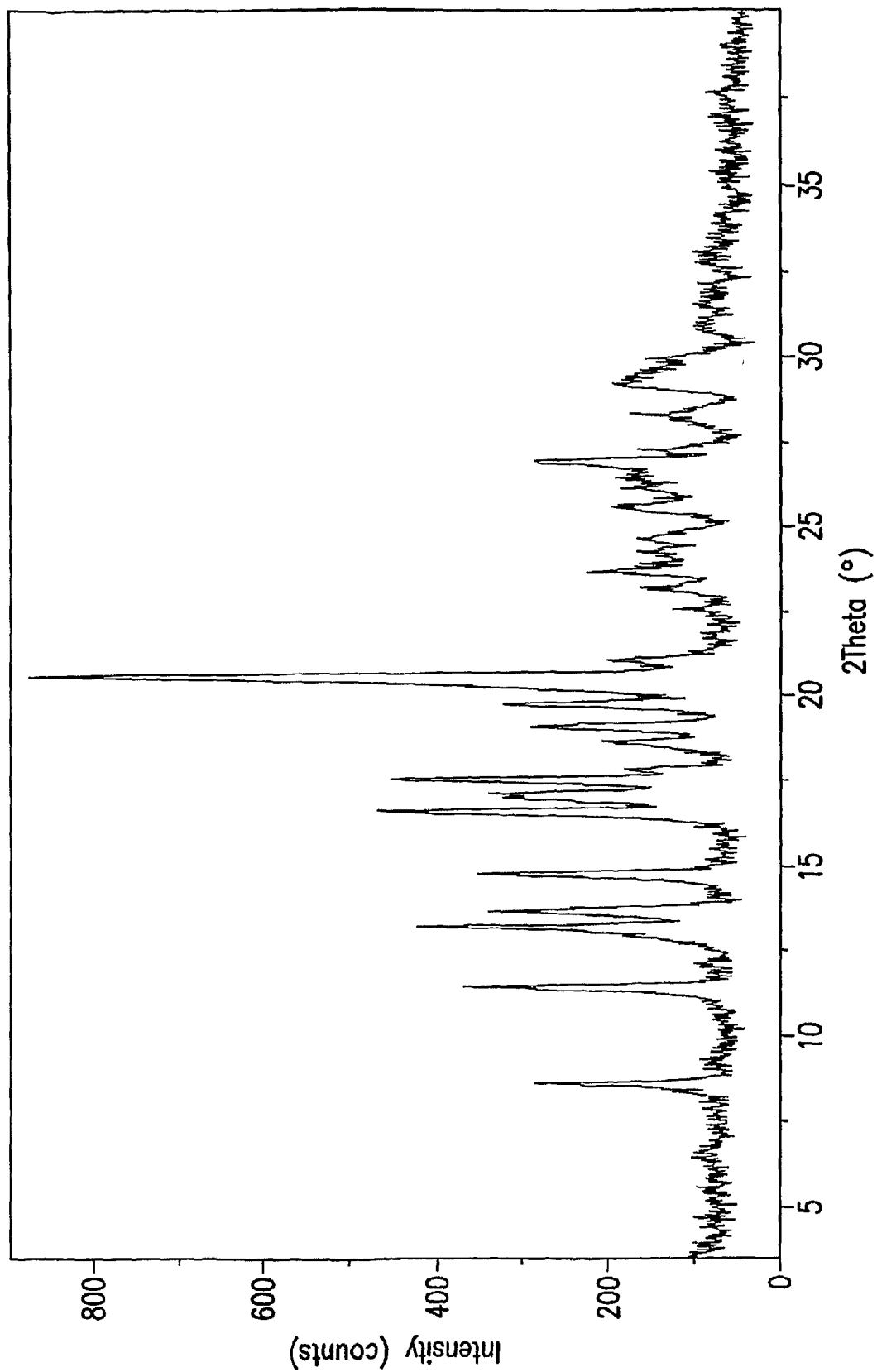
FIG. 6 is a characteristic X-ray diffraction pattern of the crystalline hemi-hydrate bis HCl salt of Compound I.

The crystalline hemi-hydrate bis HCl salt of N-{(1S)-1-[2-(1-{[(3S,4R)-1-tert-butyl-4-(2,4-difluorophenyl) pyrrolidin-3-yl]carbonyl}piperidin-4-yl)-5-chlorophenyl]ethyl}acetamide (Compound I) is characterized by characteristic diffraction peaks obtained from an X-ray powder diffraction pattern corresponding to spectral d-spacings of 5.3, 5.1, and 4.3 angstroms; is further characterized by the d-spacings of 7.8, 6.7, and 6.0 angstroms; and is even further characterized by the d-spacings of 6.5, 5.2, and 4.5 angstroms (see FIG. 6).

Figure 7:
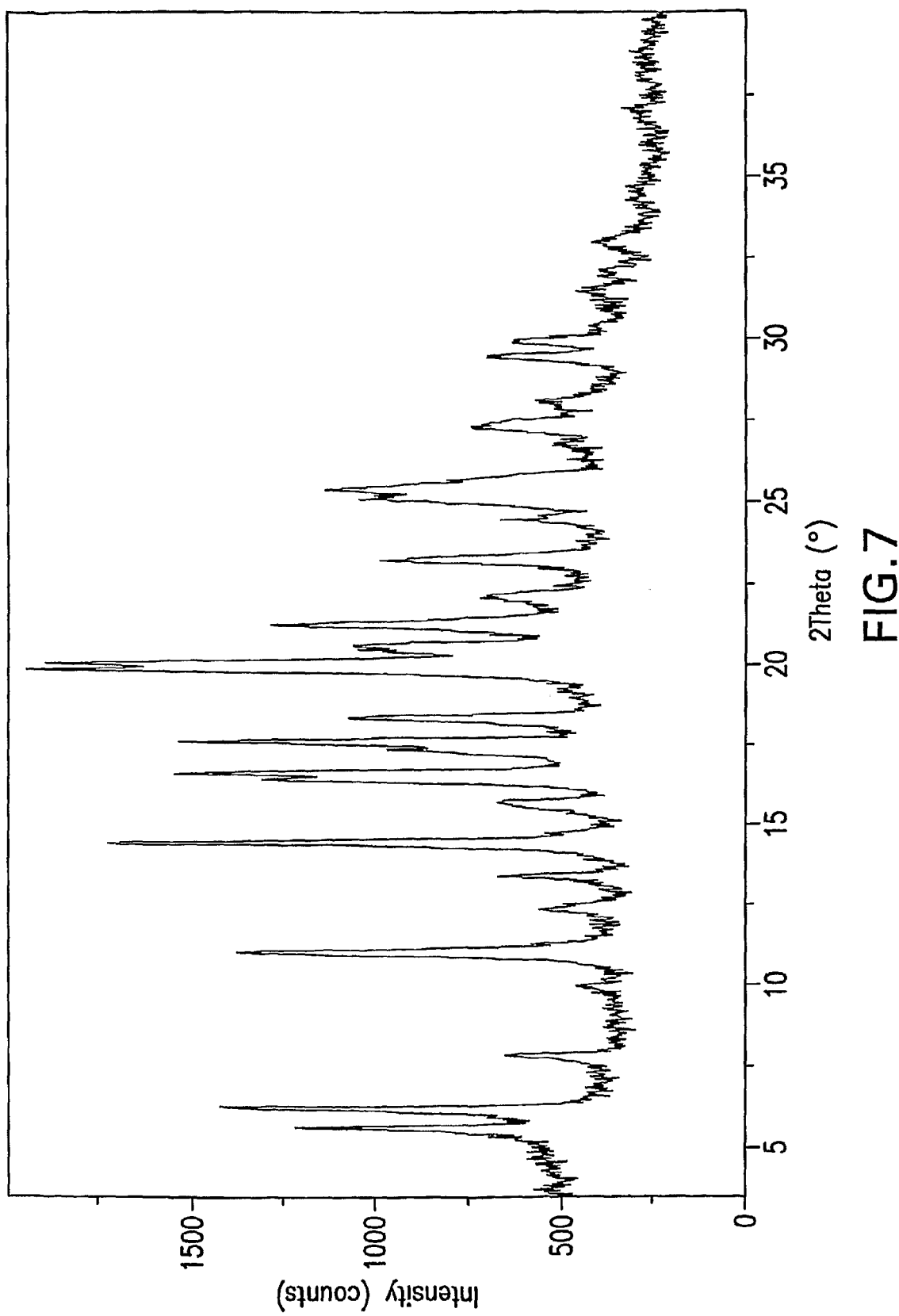
FIG. 7 is a characteristic X-ray diffraction pattern of the crystalline bis HCl salt 2-Propanol/Isopropyl Acetate co-solvate of the bis HCl salt of Compound I.

The crystalline 2-Propanol/Isopropyl Acetate co-solvate of the bis HCl salt of N-{(1S)-1-[2-(1-{[(3S,4R)-1-tert-butyl-4-(2,4-difluorophenyl) pyrrolidin-3-yl]carbonyl}piperidin-4-yl)-5-chlorophenyl]ethyl}acetamide (Compound I) is characterized by characteristic diffraction peaks obtained from an X-ray powder diffraction pattern corresponding to spectral d-spacings of 6.1, 4.5, and 4.4 angstroms; is further characterized by the d-spacings of 8.1, 5.3, and 5.1 angstroms; and is even further characterized by the d-spacings of 14.1, 5.4, and 4.2 angstroms (see FIG. 7).

Figure 8:
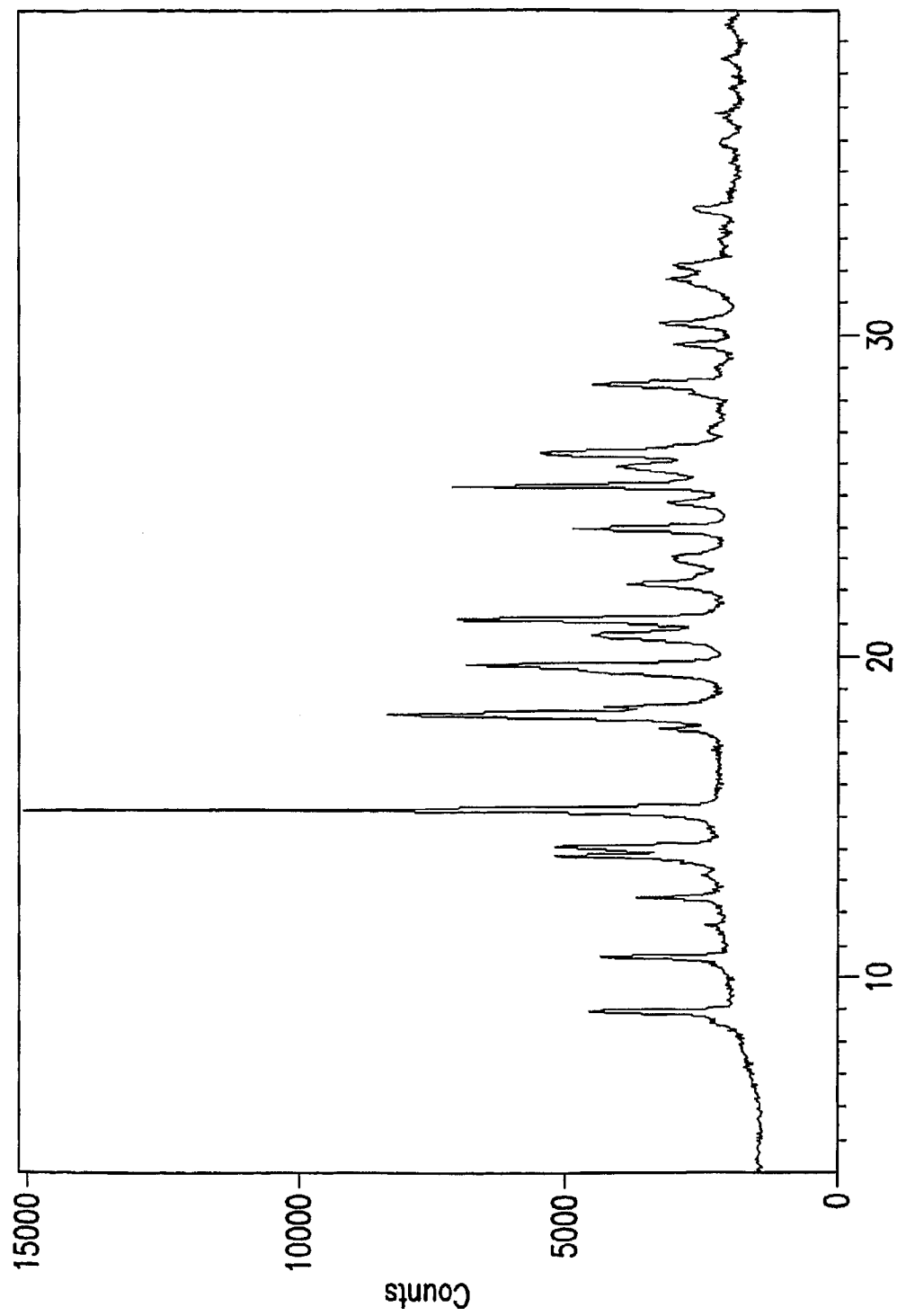
FIG. 8 is a characteristic X-ray diffraction pattern of the crystalline mono HBr salt of Compound I.

The crystalline mono HBR salt of N-{(1S)-1-[2-(1-{[(3S,4R)-1-tert-butyl-4-(2,4-difluorophenyl) pyrrolidin-3-yl]carbonyl}piperidin-4-yl)-5-chlorophenyl]ethyl}acetamide (Compound I) is characterized by characteristic diffraction peaks obtained from an X-ray powder diffraction pattern corresponding to spectral d-spacings of 9.0, 15.2, and 19.7 angstroms; is further characterized by the d-spacings of 10.6, 18.2, and 25.3 angstroms; and is even further characterized by the d-spacings of 21.1, 26.3, and 28.5 angstroms (see FIG. 8).

The present invention further provides a pharmaceutical composition comprising a crystalline salt, hydrate, solvate, polymorph, or a mixture thereof, of N-{(1S)-1-[2-(1-{[(3S,4R)-1-tert-butyl-4-(2,4-difluorophenyl) pyrrolidin-3-yl]carbonyl}piperidin-4-yl)-5-chlorophenyl]ethyl}acetamide (Compound I), and a pharmaceutically acceptable carrier. In one embodiment of the present invention, the composition contains the crystalline hydrate mono HCl salt of Compound I. In a class of this embodiment, the crystalline hydrate mono HCl salt of Compound I is in substantially pure form. In another class of this embodiment, the crystalline hydrate mono HCl salt of compound I contains about 0 mole percent to about 7 mole percent of water. In a subclass of this class, the crystalline hydrate mono HCl salt of compound I contains about 0.01 mole percent to about 6 mole percent of water. In another embodiment of the present invention, the composition contains the crystalline anhydrous mono HCl salt Form I. In a class of this embodiment, the crystalline anhydrous mono HCl salt Form I is in substantially pure form. In another embodiment of the present invention, the composition contains the crystalline anhydrous mono HCl salt Form II. In a class of this embodiment, the crystalline anhydrous mono HCl salt Form II is in substantially pure form. In another embodiment of the present invention, the composition contains the crystalline bis HCl salt Form I. In a class of this embodiment, the crystalline bis HCl salt Form I is in substantially pure form. In another embodiment of the present invention, the composition contains the crystalline bis HCl salt Form II. In a class of this embodiment, the crystalline bis HCl salt Form II is in substantially pure form. In another embodiment of the present invention, the composition contains the crystalline hemi-hydrate bis HCl salt. In a class of this embodiment, the crystalline hemi-hydrate bis HCl salt is in substantially pure form. In another embodiment of the present invention, the composition contains the crystalline 2-propanol/isopropyl acetate co-solvate of the bis HCl salt. In a class of this embodiment, crystalline 2-propanol/isopropyl acetate co-solvate of the bis HCl salt is in substantially pure form. In another embodiment of the present invention, the composition contains the crystalline mono HBr salt. In a class of this embodiment, the crystalline mono HBr salt is in substantially pure form. In another embodiment of the present invention, the crystalline salt of Compound I is selected from the group consisting of perchlorate salt, tetrafluoroborate, hexafluoroantimonate, and hexafluorophosphate. In another embodiment of the present invention, the solvate of the free base of Compound I is selected from the group consisting of methanol, ethanol, isopropanol, isopropyl acetate and water.

Another aspect of the present invention provides pharmaceutical compositions which comprise a crystalline salt, solvate, hydrate and/or polymorph of Compound I, and a pharmaceutically acceptable carrier, and optionally other therapeutic ingredients.

The present invention also provides a method for the treatment, control and/or prevention of obesity, diabetes mellitus, and obesity-related disorders in a subject in need thereof comprising administering a therapeutically effective amount of a hydrate, salt, solvate, or polymorph of Compound I to the subject in need thereof. The present invention also provides a method for treating or preventing obesity in a subject in need thereof comprising administering a therapeutically or prophylactically effective amount of the crystalline hydrate mono hydrochloride salt of Compound I to the subject in need thereof. The present invention also provides a method for treating or preventing diabetes mellitus in a subject in need thereof comprising administering a therapeutically or prophylactically effective amount of the crystalline hydrate mono hydrochloride salt of Compound I to the subject in need thereof. The present invention also provides a method for treating or preventing an obesity-related disorder in a subject in need thereof comprising administering a therapeutically or prophylactically effective amount of the crystalline hydrate mono hydrochloride salt of Compound I to the subject in need thereof.

The present invention also provides a method for the treatment, control and/or prevention of male sexual dysfunction, female sexual dysfunction, male erectile dysfunction, in a subject in need thereof comprising administering a therapeutically effective amount of a hydrate, salt, solvate, or polymorph of Compound I to the subject in need thereof. The present invention also provides a method for treating or preventing male sexual dysfunction, including male erectile dysfunction, in a subject in need thereof comprising administering a therapeutically or prophylactically effective amount of the crystalline hydrate mono hydrochloride salt of Compound I to the subject in need thereof. The present invention also provides a method for treating or preventing female sexual dysfunction in a subject in need thereof comprising administering a therapeutically or prophylactically effective amount of the crystalline hydrate mono hydrochloride salt of Compound I to the subject in need thereof.

The present invention further provides the use of the crystalline hydrate mono hydrochloride salt of Compound I for the manufacture of a medicament useful for the treatment or prevention of in a subject in need thereof.

The present invention further provides for the use of the hydrates, salts, solvates, and polymorphs of Compound I for the manufacture of a medicament for the treatment, control and/or prevention of obesity, diabetes, and obesity related disorders. The present invention further provides for the use of the hydrates, salts, solvates, and polymorphs of Compound I for the manufacture of a medicament for the treatment, control and/or prevention of male sexual dysfunction, female sexual dysfunction, and male erectile dysfunction. The present invention further provides the use of the crystalline hydrate mono hydrochloride salt of Compound I for the manufacture of a medicament useful for the treatment or prevention of obesity in a subject in need thereof. The present invention further provides the use of the crystalline hydrate mono hydrochloride salt of Compound I for the manufacture of a medicament useful for the treatment or prevention of diabetes mellitus in a subject in need thereof. The present invention further provides the use of the crystalline hydrate mono hydrochloride salt of Compound I for the manufacture of a medicament useful for the treatment or prevention of an obesity-related disorder in a subject in need thereof. The present invention further provides the use of the crystalline hydrate mono hydrochloride salt of Compound I for the manufacture of a medicament useful for the treatment or prevention of female sexual dysfunction in a subject in need thereof. The present invention further provides the use of the crystalline hydrate mono hydrochloride salt of Compound I for the manufacture of a medicament useful for the treatment or prevention of male sexual dysfunction, including male erectile dysfunction in a subject in need thereof.

The present invention also provides a process for the preparation of Compound I:

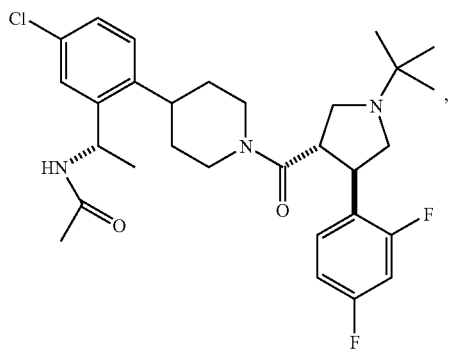

(I)

or a salt, hydrate, solvate, or polymorph thereof, comprising the steps of:
(a) coupling the compound of formula (II)

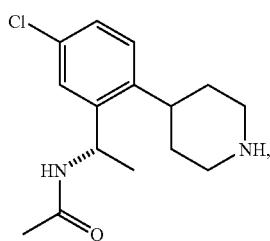

(II)

or a salt thereof, with a compound of formula (III)

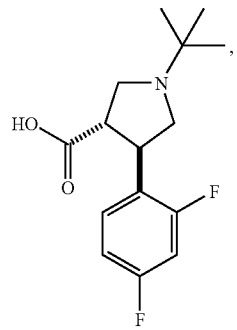

(III)

or a salt thereof,
in the presence of a coupling agent; and
(b) isolating the resulting product.

In one embodiment of the present invention, the salt of compound (II) is a hydrochloride salt.

In another embodiment of the present invention, the coupling reagent of step (a) is selected from the group consisting of: EDC, CDI, HATU, PyBOP, and $SOCl_2$. In a class of this embodiment, the coupling reagent is selected from the group consisting of: CDI and $SOCl_2$. In a subclass of this class, the coupling reagent is CDI. In another subclass of this class, the coupling reagent is $SOCl_2$.

In another embodiment of the present invention, step (a) further comprises a base. In a class of this embodiment, the base of step (a) is selected from the group consisting of 2-hydroxypyridine N-oxide, triethylamine, N,N-diisopropylethylamine, and N-methylmorpholine. In another class of this embodiment, the base is selected from the group consisting of: 2-hydroxypyridine N-oxide, and triethylamine. In a subclass of this class, the base is 2-hydroxypyridine N-oxide. In another subclass of this class, the base is triethylamine. In another embodiment of the present invention, the coupling reagent is 1,1 carbonyldiimidazole, and the base is triethylamine.

In another embodiment of the present invention, the reaction in step (a) is run in a solvent selected from the group consisting of THF, acetonitrile, N,N-dimethylformamide, and methylene chloride, or a mixture thereof. In a class of this embodiment, the solvent is selected from the group consisting of: THF, and acetonitrile, or a mixture thereof. In a subclass of this class, the solvent is THF. In another subclass of this class, the solvent is acetonitrile.

In another embodiment of the present invention, the reaction in step (a) is run at a temperature of between about −10° C. to about 50° C. In a class of this embodiment, the reaction in step (a) is run between about 0° C. and about 40° C. In another class of this embodiment, the reaction in step (a) is run at about 0° C.

The compounds in the processes of the present invention include stereoisomers, such as optical isomers, diastereomers and geometerical isomers, or tautomers depending on the mode of substitution. The present invention is meant to comprehend all such isomeric forms of Compound I in the present invention, and their mixtures.

The salts, solvates, hydrates and polymorphs of Compound I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray. The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

The salts, solvates, hydrates and polymorphs of Compound I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably the salt, solvate, hydrate and/or polymorph of Compound I is administered orally. The effective dosage of active ingredient employed may vary depending on the particular compound employed, the mode of administration, the condition being treated and the severity of the condition being treated. Such dosage may be ascertained readily by a person skilled in the art.

When treating obesity, diabetes mellitus, male sexual dysfunction, male erectile dysfunction, female sexual dysfunction, or an obesity-related disorder, generally satisfactory results are obtained when the crystalline salt, hydrate, solvate and/or polymorph of Compound I is administered at a daily dosage of from about 0.001 milligram to about 100 milligrams per kilogram of animal body weight, preferably given in a single dose or in divided doses two to six times a day, or in sustained release form. In the case of a 70 kg adult human, the total daily dose will generally be from about 0.07 milligrams to about 3500 milligrams. This dosage regimen may be adjusted to provide the optimal therapeutic response.

Polymorphism can be defined as the ability of a chemical substance to exist in different crystalline structures, which are referred to as polymorphs or polymorphic forms. The term "amorphous" refers to solid forms of Compound I that have no long-range molecular order.

The term "hydrate" is meant to include all full, multiple hydrate, partial hydrates and ranges of hydrates of Compound I, including, but not limited to, the mono hydrate, hemihydrate and bis hydrate. In particular, the present invention includes the crystalline hydrate mono HCl salt of Compound I wherein the hydration is about 0 mole % to about 7 mole %, more particularly, the hydration is about 0.01 mole % to about 6 mole %. For example, typically the crystalline hydrate mono HCl salt of Compound I is in a 4% hydration state, but may contain a higher or lower percent hydration within the above range.

The term "solvate" is meant to include compound forms containing solvent molecules within the crystal structure of compound I, or solvent molecules bound to or associated with Compound I, including but not limited to methanol, ethanol, isopropanol and isopropyl acetate. The salts of Compound I refer to the pharmaceutically acceptable and common salts, including but not limited to, the mono HCl salt, the bis HCl salt, the perchlorate salt, the tetrafluoroborate salt, the hexafluoroantimonate salt, and the hexafluorophosphate salt.

The obesity-related disorders herein are associated with, caused by, or result from obesity. Examples of obesity-related disorders include overeating and bulimia, hypertension, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovary disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia, metabolic syndrome, insulin resistance syndrome, reproductive hormone abnormalities, sexual and reproductive dysfunction, such as impaired fertility, infertility, hypogonadism in males and hirsutism in females, fetal defects associated with maternal obesity, gastrointestinal motility disorders, such as obesity-related gastro-esophageal reflux, respiratory disorders, such as obesity-hypoventilation syndrome (Pickwickian syndrome), breathlessness, cardiovascular disorders, inflammation, such as systemic inflammation of the vasculature, arteriosclerosis, hypercholesterolemia, hyperuricaemia, lower back pain, gallbladder disease, gout, kidney cancer, increased anesthetic risk, left ventricular hypertrophy, Alzheimer's disease.

"Treatment" (of obesity and obesity-related disorders) refers to the administration of the compounds or combinations of the present invention to reduce or maintain the body weight of an obese subject. "Treatment" (of sexual dysfunction, including male erectile dysfunction) refers to the administration of the compounds or combinations of the present invention to restore sexual function, or male erectile function, in a subject in need thereof. "Prevention" (of obesity and obesity-related disorders) refers to the administration of the compounds or combinations of the present invention to reduce or maintain the body weight of a subject at risk of obesity. "Prevention" (of sexual dysfunction, including male erectile dysfunction) refers to the administration of the compounds or combinations of the present invention to prevent sexual dysfunction or to prevent male erectile dysfunction, in a subject at risk thereof.

The term "subject", as used herein refers to an animal, preferably a mammal, most preferably a human, who has been the object of treatment, observation or experiment. The term "subject in need thereof" refers to a subject who is in need of treatment or prophylaxis as determined by a researcher, veterinarian, medical doctor or other clinician. In one embodiment, the subject in need of treatment is an obese mammal. In another embodiment, the subject in need of treatment is an obese human with one or more obesity-related co-morbidities. In another embodiment, the subject in need of treatment is an obese human without obesity-related co-morbidities. The term "therapeutically effective amount" as used herein means the amount of the active compounds in the composition that will elicit the biological or medical response in a tissue, system, subject, or human that is being sought by the researcher, veterinarian, medical doctor or other clinician, which includes alleviation of the symptoms of the disorder being treated. The term "prophylactically effective amount" as used herein means the amount of the active compounds in the composition that will elicit the biological or medical response in a tissue, system, subject, or human that is being sought by the researcher, veterinarian, medical doctor or other clinician, which includes prevention of the symptoms of the disorder or prevention of the disorder.

X-ray powder diffraction studies are widely used to characterize molecular structures, crystallinity, and polymorphism. The X-ray powder diffraction pattern of the crystalline forms of N-{(1S)-1-[2-(1-{[(3S,4R)-1-tert-butyl-4-(2,4-difluorophenyl) pyrrolidin-3-yl]carbonyl}piperidin-4-yl)-5-chlorophenyl]ethyl}acetamide were generated on a Philips Analytical X'Pert PRO X-ray Diffraction System with PW3040/60 console. A PW3373/00 ceramic Cu LEF X-ray tube K-Alpha radiation was used as the source. The margin of error in the angle 2 theta values of the X-ray powder diffraction pattern of the crystalline forms of N-{(1S)-1-[2-(1-{[(3S,4R)-1-tert-butyl-4-(2,4-difluorophenyl) pyrrolidin-3-yl]carbonyl}piperidin-4-yl)-5-chlorophenyl]ethyl}acetamide is approximately ±0.1°.

In addition to the X-ray powder diffraction patterns described above, the crystalline forms of N-{(1S)-1-[2-(1-{[(3S,4R)-1-tert-butyl-4-(2,4-difluorophenyl) pyrrolidin-3-yl]carbonyl}piperidin-4-yl)-5-chlorophenyl]ethyl}acetamide were further characterized by their solid-state carbon-13 and fluorine-19 nuclear magnetic resonance (NMR) spectra. The solid-state carbon-13 NMR spectrum was obtained on a Bruker DSX 400WB NMR system using a Bruker 4 mm double resonance CPMAS probe. The carbon-13 NMR spectrum utilized proton/carbon-13 cross-polarization magic-angle spinning with variable-amplitude cross polarization. The sample was spun at 15.0 kHz, and a total of 512 scans were collected with a recycle delay of 7 seconds. A line broadening of 40 Hz was applied to the spectrum before FT was performed. Carbon-13 chemical shifts are reported on the TMS scale using the carbonyl carbon of glycine (176.03 p.p.m.) as a secondary reference.

The solid-state fluorine-19 NMR spectrum was obtained on a Bruker DSX 400WB NMR system using a Bruker 4 mm CRAMPS probe. The fluorine-19 NMR spectrum utilized a simple pulse-acquire pulse program. Fluorine-19 chemical shifts are reported using poly(tetrafluoroethylene) (teflon) as an external secondary reference which was assigned a chemical shift of −122 ppm.

DSC data were acquired using TA Instruments DSC 2920 or equivalent instrumentation. Between 1 and 6 mg sample is weighed into an open pan. This pan is then crimped and placed at the sample position in the calorimeter cell. An empty pan is placed at the reference position. The calorimeter cell is closed and a flow of nitrogen is passed through the cell. The heating program is set to heat the sample at a heating rate of 10° C./min to a temperature of approximately 250° C. The heating program is started. When the run is completed, the data are analyzed using the DSC analysis program contained in the system software.

TGA data were acquired using TA Instruments TGA 2950 or equivalent instrumentation. Between 5 and 20 mg sample is weighed into a platinum pan. The furnace is raised and a flow of nitrogen is passed over the sample. The heating program is set to heat the sample at a heating rate of 10° C./min to a temperature of approximately 250° C. The heating program is started. When the run is completed, the data are analyzed using the delta Y function in the analysis program contained in the system software. The percent weight loss by the sample is calculated from the onset of the heating program to the melt/decomposition of the sample.

In the scheme and examples below, various reagent symbols and abbreviations have the following meanings: CDI is 1,1-carbonyldiimidazole; DMF is dimethylformamide; EtOAc is ethyl acetate; EtOH is ethanol; EDC is 1-(3-dimethylaminopropyl)-3-ethylcarbodiimide HCl; $CH_3CN$ is acetonitrile; eq or equiv is equivalents; g is grams; h or hr is hour(s); $H_2$ is hydrogen; HATU is O-(7-azabenzotriazol-1-yl)-1,1,3,3-tetramethyluronium hexafluorophosphate; HBr is hydrobromic, HCl is hydrochloric acid, HPLC is high pressure liquid chromatography; mmHg is millimeters of mercury; IPAC is isopropyl acetate; i-PrOH is isopropanol; kg is kilograms; L is liters; M is molar; mmol is millimole; mL is milliliters; Me is methyl; MeOH is methanol, mol is moles; N is normal; $N_2$ is nitrogen; NaCl is sodium chloride; $NaHCO_3$ is sodium bicarbonate; NaOH is sodium hydroxide; $Na_2SO_4$ is sodium sulfate; NMR is nuclear magnetic resonance; Ph (ph) is phenyl; psi is pounds per square inch; PyBOP is bromo-tris-pyrrolidino-phosphonium hexafluorophosphate; RT is room temperature; and THF is tetrahydrofuran; and % is percent.

The process is exemplified with the preparation of N-{(1S)-1-[2-(1-{[(3S,4R)-1-tert-butyl-4-(2,4-difluorophenyl)pyrrolidin-3-yl]carbonyl}piperidin-4-yl)-5-chlorophenyl]ethyl}-acetamide (1-3, Compound I) as shown in Scheme 1.

Scheme 1

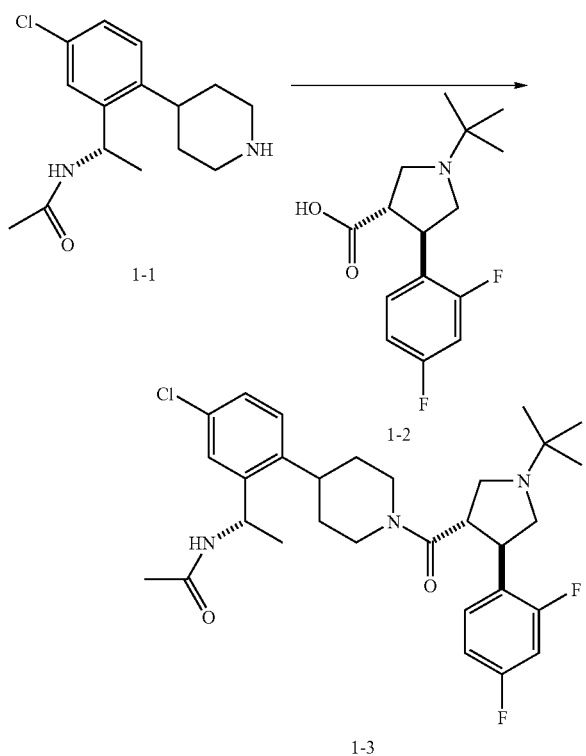

As shown in Scheme 1, compound 1-3 is prepared by coupling piperidine 1-1 with pyrrolidine acid 1-2 in the presence of a coupling agent, such as EDC, CDI, HATU or PyBop, and a base such as 2 hydroxy pyridine N-oxide, triethylamine, or N-methylmorpholine, in a solvent, such as THF, acetonitrile, or DMF, at a temperature of about 0° C. to about 40° C.

A representative experimental procedure utilizing the novel process is detailed below. The following Example is provided to illustrate the invention and is not to be construed as limiting the scope of the invention in any manner.

Example 1
Preparation of the Free Base of Compound (1-3)

Step A: Preparation of Compound 1-1
  Piperidine 1-1 may be prepared as shown in WO 02/068388 and US 2003/0225060.
Step B: Preparation of Compound 1-2
  Pyrrolidine acid 1-2 may be prepared as shown in WO 02/068388 and US 2003/0225060.
Step C: Preparation of the Free Base of Compound I (1-3)

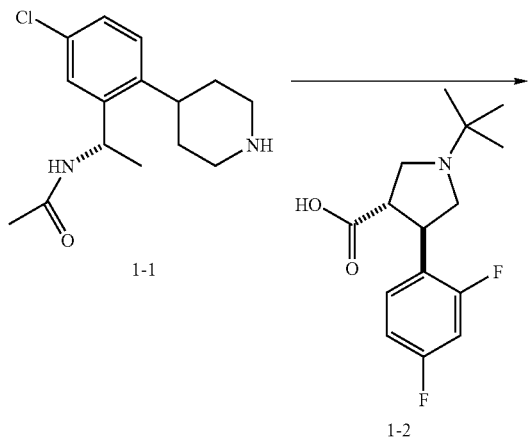

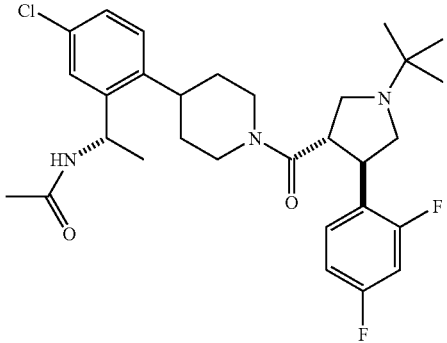

A heterogenous solution of pyrrolidine acid 1-2 (2.0 kg, 7.06 mol) in acetonitrile (10 L) was slurried, warmed to 40° C., and then flushed with acetonitrile at constant volume to remove isopropyl alcohol. The solution was warmed to 40° C., then CDI (1.14 kg, 7.06 mol) was added in three portions, and the resulting homogenous solution was aged for 30 minutes and then assayed by quenching into an acetonitrile solution of piperidine. Once deemed complete the solution was cooled to RT.

A mixture of piperidine 1-1 (2.2 kg; 7.06 mol) in acetonitrile (22 mL) was cooled to 0° C. To this mixture was added triethylamine (3.57 kg, 4.9 L, 35.3 mol), and the resulting slurry was aged for 1 hour. To this mixture was added the solution of pyrrolidine acid 1-2 from Step A while keeping the internal reaction temperature below 5° C. The resulting mixture was allowed to warm to room temperature and stirred overnight. To this mixture was added 5% brine (10 L) and isopropyl acetate (10 L). After settling, the aqueous layer was removed and the organic layer was washed with 5% brine (10 mL). The resulting organic layer was flushed with isopropyl acetate to remove any residual acetonitrile and triethylamine to give compound 1-3, which may further be converted to the HCl or HBr salt. The free base of Compound I (1-3) may also be crystallized by dissolving the mono HCl salt in 1:1 methanol/water and titrating with 2 equivalents of NaOH. The resulting white precipitate is aged overnight on a slurry wheel. This procedure can be repeated using 1:1 ethanol/water and 1:1 isopropanol/water.

The free base of Compound I, in acetonitrile, exists as a 50:50 rotameric mixture of the piperidine acetamide bond; both rotamers are reported in the proton data: $^1$H-NMR (500.13 MHz, CD$_3$CN), δ 7.55-7.47 (om, 1H), 7.32 (s, 1H), 7.21-7.17 (om, 1.5H), 6.99 (d, J=8.7, 0.5H), 6.98-6.81 (om, 3H), 5.26-5.19 (om, 1H), 4.66 (br d, J=13.9, 0.5H), 4.62 (br d, J=13.9, 0.5H), 3.99-3.90 (om, 2H), 3.41 (m, 0.5H), 3.32 (m, 0.5H), 3.24 (t, J=9.1, 0.5H), 3.19 (t, J=8.7, 0.5H), 3.14-3.04 (om, 2.5H), 3.00 (m, 0.5H), 2.83-2.74 (om, 2H), 2.59 (m, 1H), 1.97-1.93 (om, 0.5H), 1.86-1.84 (om, 0.5H), 1.84 (s, 3H), 1.71-1.57 (om, 1H), 1.52 (d J=12.7, 0.5H), 1.39 (m, 0.5H), 1.34 (d, J=6.8, 1.5H), 1.33 (d, J=6.8, 1.5H), 1.25 (m, 0.5H), 1.16 (m, 0.5H), 1.09 (br s, 9H) ppm.

Example 2

Preparation of the Amorphous Mono HCl Salt of Compound I (1-4)

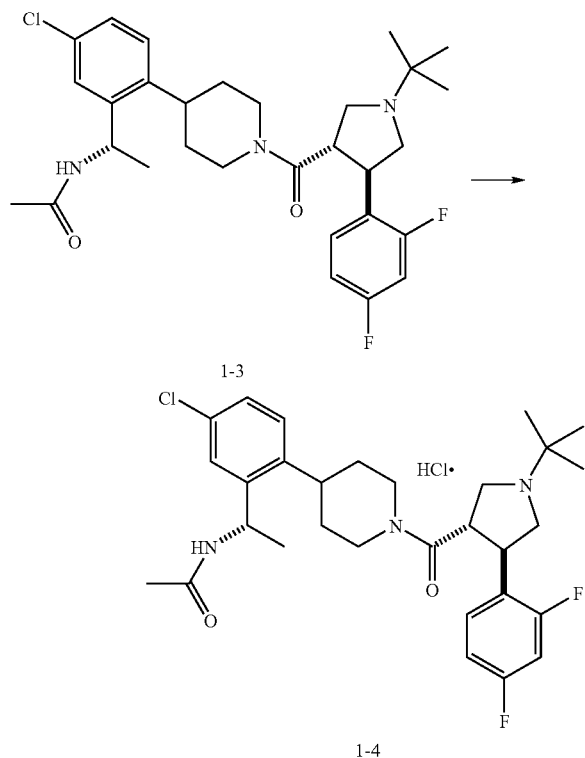

Method The amorphous mono HCl salt of Compound I (1-3 may be prepared as shown in WO 02/068388 and US 2003/0225060.

The amorphous mono HCl salt of compound I (1-4) exhibited no characteristic X-ray diffraction pattern peaks corresponding to d-spacings. The differential scanning calorimetry (DSC) curve for compound 1-4 displays a step transition corresponding to the glass transition of the material with an inflection temperature of 159° C. and a delta Cp of 0.4 J/g*C.

Example 3

Preparation of Crystalline Anhydrous Mono HCl Salt (Form 1) of Compound I (1-5)

Method 1 Drying the crystalline hydrate mono HCl salt of Compound I (1-7) under vacuum with a nitrogen sweep at a temperature of about 40-60 C. yields the crystalline anhydrous mono HCl salt Form I of Compound I (1-5).

Method 2 Drying the crystalline hydrate mono HCl salt of Compound I (1-7) at a temperature over about 4° C. and relative a humidity less than about 10% yields the crystalline anhydrous mono HCl salt Form I of Compound I (1-5). The crystalline hydrate mono HCl salt of Compound I (1-7) converts to the crystalline anhydrous mono HCl salt Form I of Compound I (1-5) by means of a continuous change; as the crystalline hydrate is dried, the x-ray diffraction pattern, solid-state carbon-13 CPMAS, and solid-state fluorine-19 MAS patterns merge from the crystalline hydrate to crystalline anhydrous Form I. Incomplete conversion to the anhydrous form I will yield a unique phase, not merely a mixture of crystalline anhydrous form I and crystalline hydrate.

Method 3 Crystalline anhydrous mono HCl salt Form II (1-6) converts to crystalline anhydrous mono HCl salt Form I (1-5) at room temperature.

The crystalline anhydrous mono HCl Salt (Form I) of compound I (1-5) is characterized by the X-ray diffraction pattern shown in FIG. 2. The crystalline anhydrous mono HCl salt Form I of Compound I (1-5) exhibited characteristic X-ray diffraction pattern peaks corresponding to d-spacings of 6.3, 6.0, and 4.6 angstroms; is further characterized by the d-spacings of 10.0, 8.2, and 5.8 angstroms; and is even further characterized by the d-spacings of 8.5, 6.5, and 4.4 angstroms. The crystalline anhydrous mono HCl salt Form I of Compound I (1-5) can be identified by any one of the following d-spacings, or any one of the following groups of d-spacings:

a) 6.3, 6.0, and 4.6 angstroms;

b) 10.0, 8.2, and 5.8 angstroms; and c) 8.5, 6.5, and 4.4 angstroms.

The crystalline anhydrous mono HCl Salt Form I of compound I (1-5) is further characterized the solid-state carbon-13 CPMAS NMR spectrum chemical shift values of 168.4, 164.8, and 149.1 p.p.m.; and is further characterized by chemical shift values of 148.5, 60.4, and 23.7 p.p.m. The sample was spun at 15.0 kHz, a total of 512 scans were collected with a recycle delay of 7 seconds; and a line broadening of 40 Hz was applied to the spectrum before FT was performed. Additionally, the crystalline anhydrous mono HCl Salt Form I of compound I (1-5) is characterized by the solid-state fluorine-19 MAS NMR spectrum chemical shift values of −105.5, −109.9, and −107.9 p.p.m. The solid-state fluorine-19 NMR spectrum samples were spun at 15.0 kHz, a total of 128 scans were collected with a recycle delay of 1 second; and a line broadening of 100 Hz was applied to the spectrum before FT was performed.

Example 4

Preparation of Crystalline Anhydrous Mono HCl Salt (Form II) of Compound I (1-6)

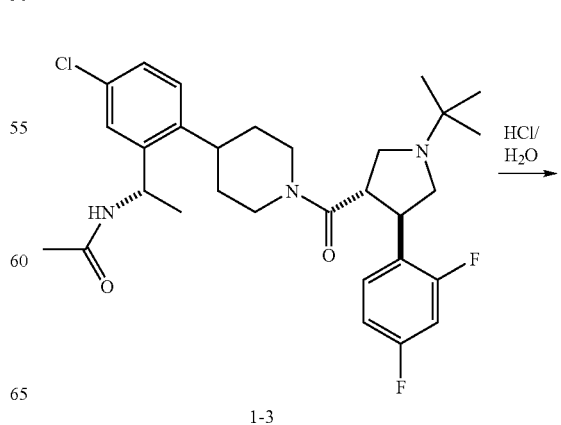

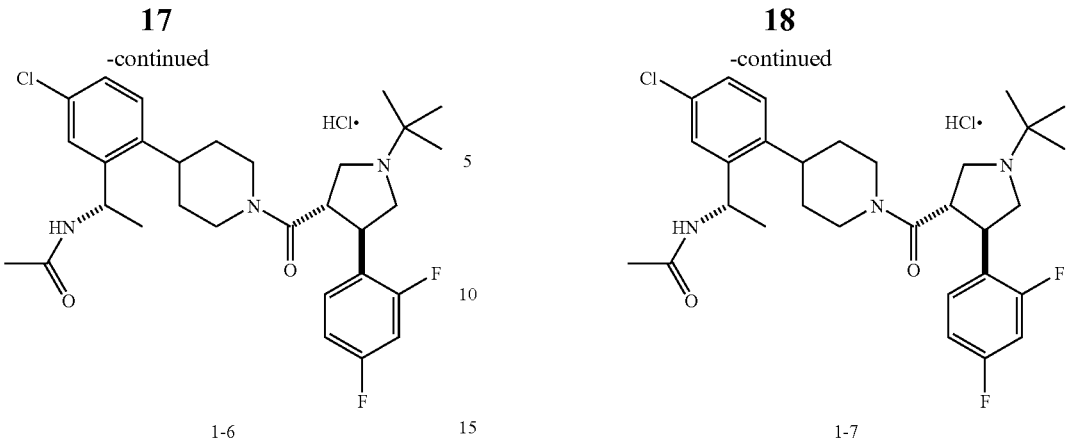

1-6

1-7

Method Heating the crystalline anhydrous mono HCl salt Form I of Compound I (1-5) at a temperature greater than about 130° C. for about one hour yields the crystalline anhydrous mono HCl salt Form II of Compound I (1-6). The crystalline anhydrous mono HCl salt Form I of Compound I (1-5) converts to the crystalline anhydrous mono HCl salt Form II of Compound I (1-6) by means of a continuous change; as Form I is heated to temperatures greater than 130° C., the x-ray diffraction pattern merges from Form I to Form II. Incomplete conversion to the Form I results in a unique phase, not merely a mixture of Form I and Form II.

The crystalline anhydrous mono HCl salt Form II of Compound I (1-6) is characterized by the X-ray diffraction pattern shown in FIG. 3. The crystalline anhydrous mono HCl salt Form II of Compound I (1-6) exhibited characteristic diffraction peaks corresponding to d-spacings of 8.3, 6.4, and 5.9 angstroms; is further characterized by the d-spacings of 9.9, 4.9 and 4.5 angstroms; and is even further characterized by the d-spacings of 7.6, 4.3, and 4.2 angstroms. The crystalline anhydrous mono HCl salt Form II of Compound I (1-6) can be identified by any one of the following d-spacings, or any one of the following groups of d-spacings:

a) 8.3, 6.4, and 5.9 angstroms angstroms;
b) 9.9, 4.9 and 4.5 angstroms; and
c) 7.6, 4.3, and 4.2 angstroms.

Example 5

Preparation of Crystalline Hydrate Mono HCl Salt of Compound I (1-7)

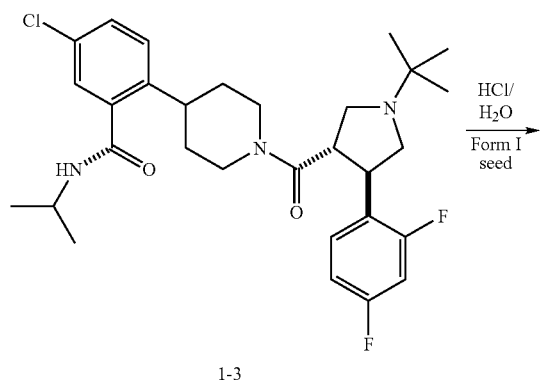

1-3

Method 1 A solution of compound 1-3 from Example 1 (14.6 g, 26.7 mmol) in isopropyl acetate (91 ml, at 160 g/L) was agitated in vessel 1 at 15-25° C., and 0.5 N HCl/H₂O solution (54.4 mL, 27.2 mmol) was added. The mixture was aged for 5-10 minutes with agitation followed by settling without agitation. The aqueous layer was removed and transferred to vessel 2. 20 ml of deionized water were charged to vessel 1, as a rinse of the isopropyl acetate layer. After agitating the isopropyl acetate-deionized water mixture for about 5 minutes, the aqueous layer was removed and combined with the aqueous layer in vessel 2. The solution in the crystallizer was heated to and kept at 40° C. with constant agitation. The crystalline seed (mono HCl salt Form I of Compound I (1-5), 0.155 g, 1 mol %) was added at 40° C., and, the mixture was aged overnight before cooling down to 20° C. The end slurry from vessel 2 was then filtered through sintered-glass filter with house-vacuum pulling from the bottom, and the resulting wet cake was washed with 10 ml de-ionized water. The washed cake was dried in the filter at room temperature overnight with house-vacuum pulling and room-air feeding to give crystalline hydrate mono-HCl salt of compound I (1-7).

Method 2 Crystalline bis HCl solid (1 kg) was added to 3 L of deionized water and agitated at room temperature for about 10 minutes to give a cloudy solution. The solution was transferred to a 10 L vessel with a jacket set at a temperature of about 30° C. Deionized water (529 mL) was used to rinse the dissolver, and then added to the 10 L vessel to give a clear solution at 30° C. (pH ~0.1). 2N aqueous NaOH solution (800 mL) was added slowly to the batch to reach pH 2.5. Seed of mono HCl hydrate or mono HCl salt Form I of compound (I) (10 g) was added. The mixture was aged at 32° C. for about 5 hours, and then at 38 C. overnight. After cooling to 20° C., the mixture was filtered, and the resulting cake was washed with 2-100 mL portions of water. The wet cake was left in the filter pot to dry under vacuum to give the crystalline hydrate mono HCl salt of compound I (1-7).

Figure 9:
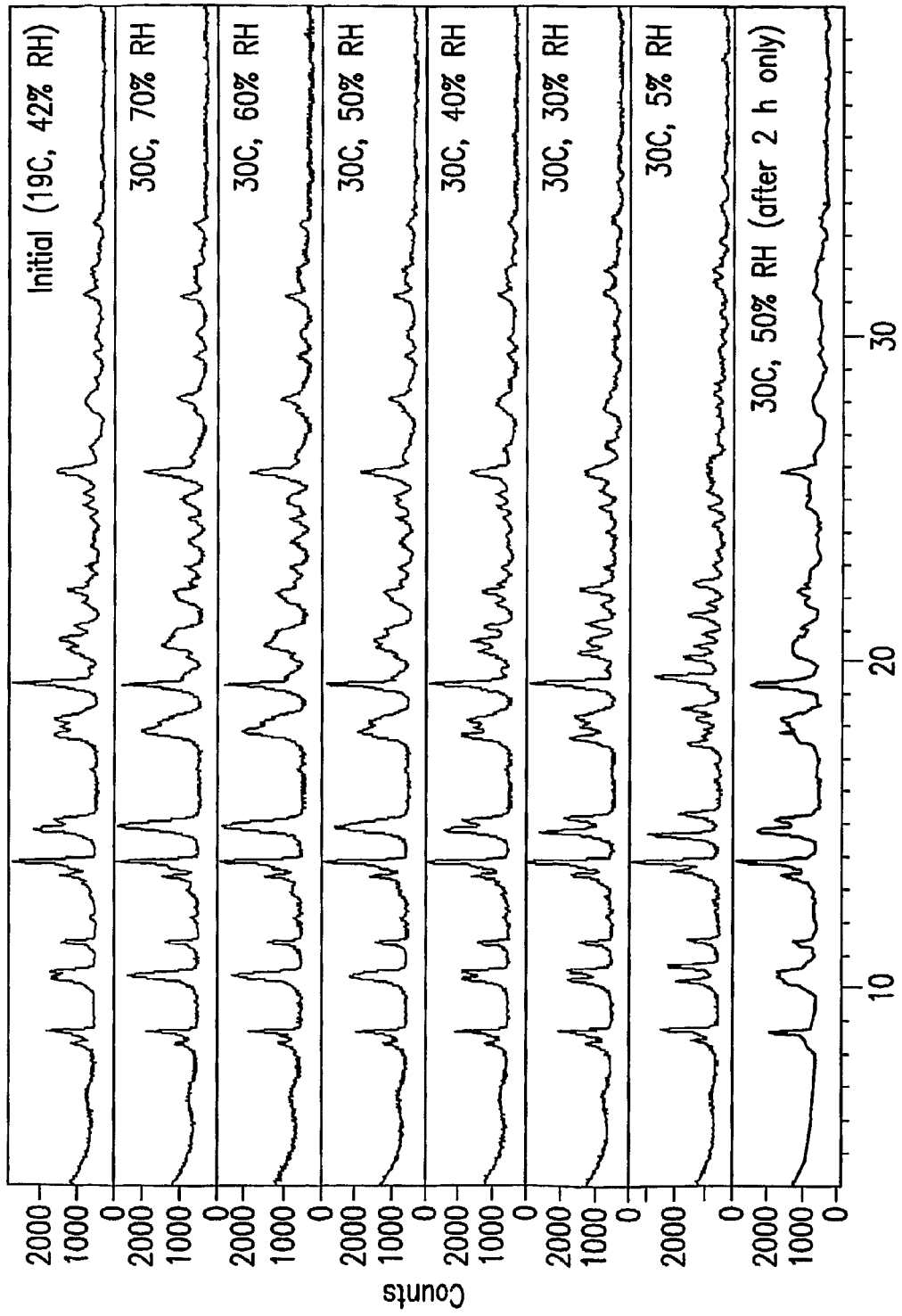
FIG. 9 shows characteristic X-ray diffraction pattern angle 2 theta value shifts due to the exposure of the crystalline anhydrous mono HCl salt Form I of Compound I to relative humidity levels between 5% and 70%, and resulting in the x-ray diffraction pattern merge from the crystalline anhydrous mono HCl Form I to the crystalline hydrate mono HCl salt of Compound I.

Method 3 The crystalline anhydrous mono HCl salt Form I of Compound I (1-5) can be converted to the crystalline hydrate mono HCl salt of compound I (1-7) by exposing Form I to a relative humidity greater than 20%; the resulting conversion occurs by means of continuous process and results in continuous structural change. As the anhydrous mono HCl salt Form I of Compound I (1-5) is exposed to relative humidity greater than 20%, the x-ray diffraction pattern (FIG. 9), solid state carbon 13 CPMAS, and solid-state fluorine-19 MAS patterns merge from the crystalline anhydrous mono HCl Form I (1-5) to the crystalline hydrate mono HCl salt (1-7). The conversion of crystalline anhydrous mono HCl salt Form I of Compound I (1-5) to the crystalline hydrate mono HCl salt of compound I (1-7) can be followed using X-ray diffraction pattern angle 2 theta values as shown in FIG. 9, wherein the angle 2 theta value of 10.4°-11.0° splits into two peaks with decreasing water content, and the angle 2 theta value of 15.0° splits into two peaks with decreasing water content. Incomplete conversion to crystalline hydrate mono HCl salt (1-7) yields a unique phase, and not merely a mixture of crystalline Form I and crystalline hydrate.

The crystalline hydrate mono HCl salt of Compound I (1-7) is a channel hydrate containing from about 0 mole % to about 7 mole % of water, more particularly containing about 0.1 mole % to about 6 mole % of water. Typically, the crystalline hydrate mono HCl salt of Compound I (1-7) contains about 4 percent water (FIG. 1). The crystalline hydrate mono HCl salt of Compound I (1-7) is characterized by the X-ray diffraction pattern shown in FIG. 1.

TABLE 1

Powder X-ray diffraction: Compound I Fumarate Salt

| 2θ(2 theta)(degrees) | Height (cts) | Intensity [%] |
| --- | --- | --- |
| 8.9 | 113.9 | 32.9 |
| 10.5 | 199.0 | 57.5 |
| 10.8 | 176.8 | 51.1 |
| 11.6 | 139.0 | 40.1 |
| 13.6 | 152.7 | 44.1 |
| 14.1 | 346.3 | 100 |
| 15.0 | 321.0 | 92.7 |
| 15.4 | 197.7 | 57.1 |
| 17.9 | 225.0 | 65.0 |
| 18.2 | 155.7 | 45.0 |
| 18.4 | 171.6 | 49.6 |
| 19.5 | 261.5 | 75.5 |
| 20.5 | 139.0 | 40.1 |
| 20.8 | 92.9 | 26.8 |
| 21.3 | 102.4 | 29.6 |
| 21.9 | 91.6 | 26.5 |
| 22.3 | 106.0 | 30.6 |
| 23.1 | 51.4 | 14.9 |
| 26.0 | 125.7 | 36.3 |
| 26.9 | 46.2 | 13.3 |
| 28.1 | 53.9 | 53.9 |
| 29.5 | 26.7 | 7.7 |
| 30.0 | 27.2 | 7.9 |
| 31.3 | 49.4 | 14.3 |
| 32.3 | 38.0 | 11.0 |
| 33.5 | 22.2 | 6.4 |

Although the crystalline hydrate mono HCl salt of Compound I (1-7) is characterized by the complete group of angle 2 theta values listed in Table 1, all the values are not required for such identification. The crystalline hydrate mono HCl salt of Compound I (1-7) can be identified by the angle theta value of about 14.1°±0.1°. The crystalline hydrate mono HCl salt of Compound I (1-7) can also be identified by any one of the following angle theta values, or any one of the following groups of angle theta values:
a) 14.1°;
b) 14.1° and 15.0°
c) 14.1°, 15.0° and 19.5°
d) 14.1°, 15.0°, 19.5° and 17.9°
e) 14.1°, 15.0°, 19.5°, 17.9° and 10.5°
f) 14.1°, 15.0°, 19.5°, 17.9°, 10.5° and 15.4°
g) 14.1°, 15.0°, 19.5°, 17.9°, 10.5°, 15.4°, 28.1°, 18.4°, 18.2°, and 13.6°.

The crystalline hydrate mono HCl salt of Compound I (1-7) exhibited characteristic diffraction peaks corresponding to d-spacings of 6.3, 5.9, and 4.6 angstroms; is further characterized by the d-spacings of 10.0, 5.8, and 3.4 angstroms; and is even further characterized by the d-spacings of 8.4, 5.0, and 4.3 angstroms. The crystalline hydrate mono HCl salt of Compound I (1-7) can be identified by any one of the following d-spacings, or any one of the following groups of d-spacings:
a) 6.3, 5.9, and 4.6 angstroms;
b) 10.0, 5.8, and 3.4 angstroms; and
c) 8.4, 5.0, and 4.3 angstroms.

The crystalline hydrate mono HCl salt of Compound I (1-7) is characterized by the solid-state carbon-13 CPMAS NMR spectrum chemical shift values of 169.6, 147.1, and 131.4 p.p.m; and is further characterized by chemical shift values of 61.7, 51.3, and 23.0 p.p.m. The solid-state carbon-13 CPMAS NMR spectrum sample was spun at 15.0 kHz, a total of 512 scans were collected with a recycle delay of 7 seconds; and a line broadening of 20 Hz was applied to the spectrum before FT was performed. The crystalline hydrate mono HCl salt of Compound I (1-7) is characterized by the solid-state fluorine-19 MAS NMR spectrum chemical shift values of −105.5 and −111.8 p.p.m. The solid-state fluorine-19 NMR spectrum samples were spun at 15.0 kHz, a total of 128 scans were collected with a recycle delay of 1 second; and a line broadening of 100 Hz was applied to the spectrum before FT was performed.

The Differential Scanning Calorimetry (DSC) curve of the crystalline hydrate mono HCl salt of Compound I (1-7) displays two endotherms: the first endotherm has a peak temperature of 110° C. and is due to the evolution of water from the lattice of the material; the second endotherm has an onset temperature of 209° C., a peak temperature of 221° C., and an enthalpy of 60 J/g and is due to the melt/decomposition of the material. The melting endotherm is integrated between baseline temperature points that are above and below the temperature range over which the endotherm is observed. The data reported are the onset temperature, peak temperature and enthalpy.

The Thermogravimetric Analysis (TGA) curve of the crystalline hydrate mono HCl salt of Compound I (1-7) displays a 2.2 percent weight loss to 200° C. Typical crystalline hydrate mono HCl salt of Compound I (1-7) can entrain between 0 and 6 percent water, and on average 4 percent water. The percent weight loss by the sample is calculated from the onset of the heating program to the melt/decomposition of the sample, approximately 200° C.

Example 6

Preparation of the Crystalline Bis HCl Salt (Form I) of Compound I (1-8)

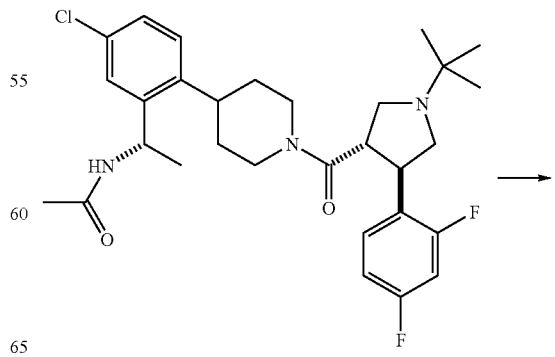

1-3

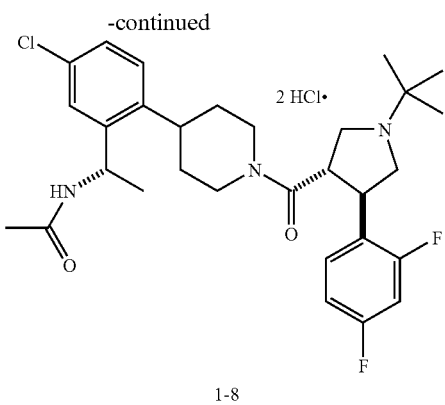

1-8

Method 1 The free base of compound 1-3 (4.24 L) was dissolved at room temperature in isopropyl acetate solution (230 g/L) under a nitrogen atmosphere. HCl in isopropyl alcohol (1.76 L, 2N) was added to the free base solution with agitation. The mixture was heated to 60° C. over 30 minutes, followed by the addition of the bis HCl salt form I of Compound I (11.0 g). The mixture was cooled to 20° C. over 1 hour to form the seed bed. The seed bed of was then heated to 60° C., followed by the simultaneous addition of the following two solution streams at constant rates over 18 hours: 1) solution A (17 L of the free base of Compound I (1-3) in isopropyl acetate solution (230 g/L) and 2) solution B (7 L of 2N HCl in isopropyl alcohol). The resulting mixture was cooled to 10-20° C. over 1 to 2 hours, then filtered through a poly filter. The resulting cake was washed with 5-10 L of isopropyl acetate at room temperature and was pre-dried in nitrogen/vacuum at atmospheric condition for a few hours. The pre-dried cake was then dried in a vacuum oven with a nitrogen sweep at 60-65° C. for 12 hours to give the his HCl salt Form I of Compound I (1-8).

Method 2 Aging a slurry of bis HCl salt 2-propanol/isopropyl acetate co-solvate of Compound I (1-11) in an organic solvent with or without high intensity agitation (e.g. a vibra-mixer), can convert the bis HCl Form II crystals to the bis HCl salt Form I crystals of Compound I (1-8).

Method 3 Aging a slurry of the bis-HCl salt form II of Compound I (1-11) in an organic solvent can convert the bis HCl form II crystals to the bis HCl salt Form I crystals of Compound I (1-8).

The crystalline bis HCl salt Form I of Compound I (1-8) is characterized by the X-ray diffraction pattern shown in FIG. 4. The bis HCl salt Form I of Compound I (1-8) exhibited characteristic diffraction peaks corresponding to d-spacings of 9.4, 4.7, and 3.7 angstroms; is further characterized by the d-spacings of 7.2, 6.3, and 4.8 angstroms; and is even further characterized by the d-spacings of 5.7, 3.4, and 3.3 angstroms. The bis HCl salt Form I of Compound I (1-8) can be identified by any one of the following d-spacings, or any one of the following groups of d-spacings:
a) 9.4, 4.7, and 3.7 angstroms;
b) 7.2, 6.3, and 4.8 angstroms; and
c) 5.7, 3.4, and 3.3 angstroms.

The crystalline bis HCl salt Form I of Compound I (1-8) is further characterized the solid-state carbon-13 CPMAS NMR spectrum chemical shift values of 178.1, 168.0, and 121.6 p.p.m; is further characterized by chemical shift values of 62.3, 35.4, and 27.9 p.p.m; and is even further characterized by chemical shift values of 19.0, 114.0, and 102.6 p.p.m. The sample was spun at 10.5 kHz, a total of 3k scans were collected with a recycle delay of 2 seconds; and a line broadening of 20 Hz was applied to the spectrum before FT was performed. Additionally, the crystalline bis HCl salt (Form I) of Compound I (1-8) is characterized by the solid-state fluorine-19 MAS NMR spectrum signals with chemical shift values of −108.0 and −111.9 p.p.m. The fluorine-19 NMR samples were spun at 15.0 kHz, a total of 128 scans were collected with a recycle delay of 5 seconds; and a line broadening of 100 Hz was applied to the spectrum before FT was performed.

The crystalline bis HCl salt Form I of Compound I (1-8) is also characterized by the Thermogravimetric Analysis (TGA) curve that displays a 0.7 percent weight loss to 100° C., and a second weight loss of 5.5 percent to 190° C. The percent weight loss by the sample is calculated from the onset of the heating program to the plateau in the curve after the loss of adsorbed water. A second percent weight loss by the sample is calculated from the plateau after the loss of adsorbed water to the plateau after the evolution of one molar equivalent of HCl. The crystalline bis HCl salt Form I of Compound I (1-8) is further characterized by the differential scanning calorimetry (DSC) curve that displays an endotherm with an onset temperature of 170° C., a peak temperature of 186° C., and an enthalpy of 101 J/g. This endotherm is due to the melt/decomposition of the material. The melting endotherm is integrated between baseline temperature points that are above and below the temperature range over which the endotherm is observed.

Example 7

Preparation of the Bis HCl Salt (Form II)
2-Propanol/Isopropyl Acetate Co-solvate of
Compound I (1-9)

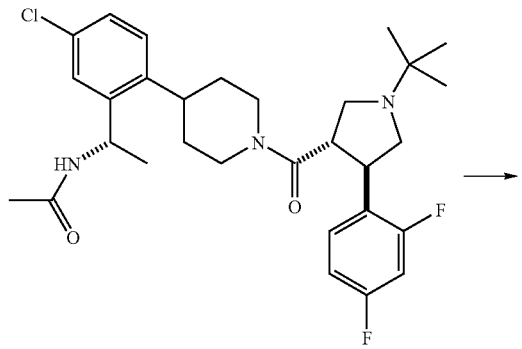

1-3

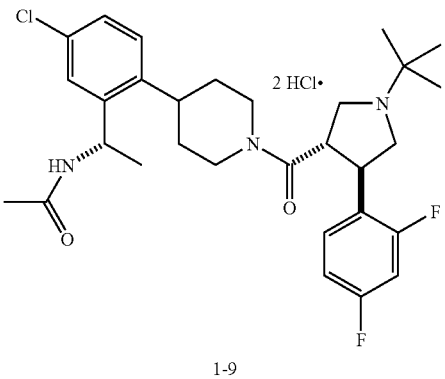

1-9

Method To a 50 mL flask was added a solution of the free base (1-3) of Compound I in isopropyl acetate (13.9 mL at 160 g/L). The solution was heated to 35° C., and HCl in isopropyl alcohol (1.33 N, 6.1 mL, 1 eq) was added in one portion. The resulting solution was heated to 60° C. and a second equivalent of 1.33N HCl in isopropyl alcohol (6.1 mL) was added in one portion. To the resulting solution at 60° C. was added seed of the bis HCl Form II of Compound I (25.2 mg). After seeding, the mixture was cooled to 20 C. over at least 1 hour, and then aged at 20° C. for a minimum of 12 hours. The mixture was filtered, and washed with isopropyl acetate (5.6 mL) to give the bis HCl salt Form II 2-propanol/isopropyl acetate co-solvate of compound I (1-9).

The crystalline 2-propanol/isopropyl acetate co-solvate of the bis HCl salt of Compound I (1-9) is characterized by the X-ray diffraction pattern shown in FIG. 7. The Compound I (1-9) exhibited characteristic diffraction peaks corresponding to d-spacings of 6.1, 4.5, and 4.4 angstroms; is further characterized by the d-spacings of 8.1, 5.3, and 5.1 angstroms; and is even further characterized by the d-spacings of 14.1, 5.4, and 4.2 angstroms. Compound I (1-9) can be identified by any one of the following d-spacings, or any one of the following groups of d-spacings:
a) 6.1, 4.5, and 4.4 angstroms;
b) 8.1, 5.3, and 5.1 angstroms; and
c) 14.1, 5.4, and 4.2 angstroms.

The crystalline 2-propanol/isopropyl acetate co-solvate of the bis HCl salt of Compound I (1-9) is further characterized the solid-state carbon-13 CPMAS NMR spectrum chemical shift values of 170.3, 140.7, and 127.4 p.p.m, with reference to a value of 176.03 p.p.m for the carbonyl peak of glycine; is further characterized by chemical shift values of 119.2, 103.5 and 66.9 p.p.m; and is even further characterized by chemical shift values of 21.1, 19.2, and 33.8 p.p.m. The sample was spun at 10.5 kHz, a total of 3k scans were collected with a recycle delay of 2 seconds; and a line broadening of 20 Hz was applied to the spectrum before FT was performed.

Example 8

Preparation of Bis HCl Salt of Compound I (1-10)

Method 1 The bis HCl salt 2-propanol/isopropyl acetate co-solvate of Compound I (1-9) was dried in a vacuum oven at 65° C. and at less than 100 mmHg overnight to give crystals of the bis HCl salt Form II of Compound I (1-10).
Method 2 Drying the hemi-hydrate of the bis HCl salt of Compound I (1-11) yields the bis HCl salt Form II crystals of Compound I (1-10).

The crystalline bis HCl salt Form II of Compound I (1-10) is characterized by the X-ray diffraction pattern shown in FIG. 5. The bis HCl salt Form II of Compound I (1-10) exhibited characteristic diffraction peaks corresponding to d-spacings of 6.9, 5.2, and 4.4 angstroms; is further characterized by the d-spacings of 5.0, 3.9 and 3.8 angstroms; and is even further characterized by the d-spacings of 6.0, 3.7, and 3.5 angstroms. The crystalline bis HCl salt Form II of Compound I (1-10) can be identified by any one of the following d-spacings, or any one of the following groups of d-spacings:
a) 6.9, 5.2, and 4.4 angstroms;
b) 5.0, 3.9 and 3.8 angstroms; and
c) 6.0, 3.7, and 3.5 angstroms.

The crystalline bis HCl salt Form II of Compound I (1-10) is further characterized the solid-state carbon-13 CPMAS NMR spectrum chemical shift values of 174.8, 172.2, and 159.6 p.p.m; is further characterized by chemical shift values of 126.5, 119.5, and 38.8 p.p.m; and is even further characterized by chemical shift values of 49.4, 61.6, and 23.7 p.p.m. The samples were spun at 10.5 kHz, a total of 3k scans were collected with a recycle delay of 2 seconds; and a line broadening of 20 Hz was applied to the spectrum before FT was performed. Additionally, the crystalline bis HCl salt Form II of Compound I (1-10) is characterized by the solid-state fluorine-19 MAS NMR spectrum chemical shift values of −110.2 and −115.4 p.p.m. The fluorine-19 NMR samples were spun at 15.0 kHz, a total of 128 scans were collected with a recycle delay of 5 seconds; and a line broadening of 100 Hz was applied to the spectrum before FT was performed.

The crystalline bis HCl salt Form II of Compound I (1-10) is also characterized by the Thermogravimetric Analysis (TGA) curve that displays a 0.4 percent weight loss to 80° C., and a second weight loss of 5.9 percent to 200° C. The percent weight loss by the sample is calculated from the onset of the heating program to the plateau in the curve after the loss of adsorbed water. A second percent weight loss by the sample is calculated from the plateau after the loss of adsorbed water to the plateau after the evolution of one molar equivalent of HCl. The crystalline bis HCl salt Form II of Compound I (1-10) is further characterized by the differential scanning calorimetry (DSC) curve that displays an endotherm with an onset temperature of 171° C., a peak temperature of 187° C., and an enthalpy of 123 J/g. This endotherm is due to the melt/decomposition of the material. The melting endotherm is integrated between baseline temperature points that are above and below the temperature range over which the endotherm is observed.

Example 9

Preparation of the Hemi-hydrate bis HCl salt of Compound I (1-11)

Exposing the bis HCl salt Form II of Compound I to humidity (e.g. 50% relative humidity overnight at room temperature) yields the crystalline hemi-hydrate bis HCl salt of Compound I (1-11).

The crystalline hemi-hydrate bis HCl salt of Compound I (1-11) is characterized by the X-ray diffraction pattern shown in FIG. 6. The crystalline hemi-hydrate bis HCl salt of Compound I (1-11) exhibited characteristic diffraction peaks corresponding to d-spacings of 5.3, 5.1, and 4.3 angstroms; is further characterized by the d-spacings of 7.8, 6.7, and 6.0 angstroms; is even further characterized by the d-spacings of 6.5, 5.2, and 4.5 angstroms. The crystalline hemi-hydrate bis HCl salt of Compound I (1-11) can be identified by any one of the following d-spacings, or any one of the following groups of d-spacings:
a) 5.3, 5.1, and 4.3 angstroms;
b) 7.8, 6.7, and 6.0 angstroms; and
c) 6.5, 5.2, and 4.5 angstroms.

The crystalline hemi-hydrate bis HCl salt of Compound I (1-11) is further characterized the solid-state carbon-13 CPMAS NMR spectrum chemical shift values of 160.1, 141.5, and 125.9 p.p.m, with reference to a value of 176.03 p.p.m for the carbonyl peak of glycine; is further characterized by chemical shift values of 51.6, 39.5, and 34.4 p.p.m; and is even further characterized by chemical shift values of 30.0, 23.7, and 43.7 p.p.m. The sample was spun at 10.5 kHz, a total of 3k scans were collected with a recycle delay of 2 seconds; and a line broadening of 20 Hz was applied to the spectrum before FT was performed. Additionally, the crystalline hemi-hydrate bis HCl salt of Compound I (1-11) is characterized by the solid-state fluorine-19 MAS NMR spectrum exhibited characteristic signals with chemical shift values of −111.0 and −115.3 p.p.m. The fluorine-19 NMR samples were spun at 15.0 kHz, a total of 128 scans were collected with a recycle delay of 5 seconds; and a line broadening of 100 Hz was applied to the spectrum before FT was performed.

The crystalline hemi-hydrate bis HCl salt of Compound I (1-11) is also characterized by a Thermogravimetric Analysis (TGA) curve that displays a 1.7 percent weight loss to 100° C., and a second weight loss of 5.7 percent to 200° C. The percent weight loss by the sample is calculated from the onset of the heating program to the plateau in the curve after the loss of adsorbed water. A second percent weight loss by the sample is calculated from the plateau after the loss of adsorbed water to the plateau after the evolution of one molar equivalent of HCl. The crystalline hemi-hydrate bis HCl salt of Compound I (1-11) is further characterized by the differential scanning calorimetry (DSC) curve that displays an endotherm with an onset temperature of 173° C., a peak temperature of 186° C., and an enthalpy of 117 J/g. This endotherm is due to the melt/decomposition of the material. The melting endotherm is integrated between baseline temperature points that are above and below the temperature range over which the endotherm is observed.

Example 10

Preparation of the Crystalline Mono HBr Salt of Compound I (1-12)

Method 250 mg/mL suspension of the free base of Compound I (1-3) in water was treated with 1.1 mole equivalents of HBr (as 48% solution in water). A clear solution was obtained which was put at 30° C. for 24 hr. The resulting crystalline material was filtered and dried in vacuum at 40 C. for 1.5 hr to give the crystalline mono HBr salt of Compound I (1-12).

The crystalline mono HBr salt of Compound I (1-12) is characterized by the X-ray diffraction pattern shown in FIG. 8. The mono HBr salt of Compound I (1-12) exhibited characteristic diffraction peaks corresponding to d-spacings of 9.0, 15.2, and 19.7 angstroms; is further characterized by the d-spacings of 10.6, 18.2, and 25.3 angstroms; and is even further characterized by the d-spacings of 21.1, 26.3, and 28.5 angstroms. The crystalline mono HBr salt of Compound I (1-12) can be identified by any one of the following d-spacings, or any one of the following groups of d-spacings:
a) 9.0, 15.2, and 19.7 angstroms;
b) 10.6, 18.2, and 25.3 angstroms; and
c) 21.1, 26.3, and 28.5 angstroms.

The crystalline mono HBr salt of Compound I (1-12) is further characterized the solid-state carbon-13 CPMAS NMR spectrum chemical shift values of 168.7, 147.6, and 127.5 p.p.m, with reference to a value of 176.03 p.p.m for the carbonyl peak of glycine; and is even further characterized by chemical shift values of 167.0, 45.8, and 20.1 p.p.m. The sample was spun at 15.0 kHz, a total of 512 scans were collected with a recycle delay of 7 seconds; and a line broadening of 40 Hz was applied to the spectrum before FT was performed.

Additionally, the crystalline mono HBr salt of Compound I (1-12) is characterized by the solid-state fluorine-19 MAS NMR spectrum signals with chemical shift values of −105.9 and −110.9 p.p.m. The solid-state fluorine-19 NMR of FIG. 3 utilized a simple pulse-acquire pulse program. The samples were spun at 15.0 kHz, a total of 128 scans were collected with a recycle delay of 1 second; and a line broadening of 100 Hz was applied to the spectrum before FT was performed.

The crystalline mono HBr salt of compound I (1-12) is further characterized by a differential scanning calorimetry (DSC) curve that displays two endotherms: the first endotherm has a peak temperature of 111° C. and is due to the evolution of water from the lattice of the material; the second endotherm has an onset temperature of 229° C., a peak temperature of 242° C., and an enthalpy of 26 J/g. This endotherm is due to the melt/decomposition of the material. The crystalline mono HBr salt of compound I (1-12) is also characterized by a Thermogravimetric Analysis (TGA) curve that displays a 2.7 percent weight loss to 200° C. due to evolution of water as confirmed by Karl Fisher titration.

What is claimed is:
1. A crystalline mono hydrochloride salt of Compound I

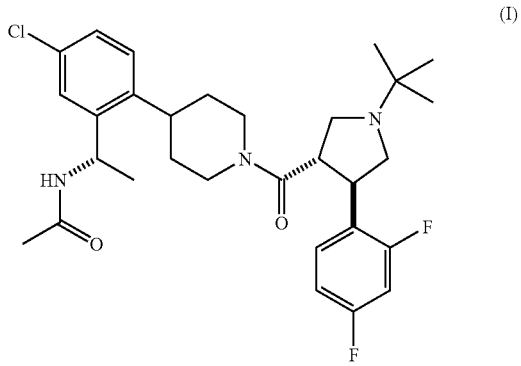

(I)

which is a hydrate comprising from about 0.1 mole percent to about 6 mole percent of water.

2. The crystalline hydrate mono hydrochloride salt of Compound I of claim 1 having an x-ray powder diffraction pattern obtained using Cu radiation containing an angle 2 theta value of 14.1°.

3. The crystalline hydrate mono hydrochloride salt of Compound I of claim 1 having an x-ray powder diffraction pattern obtained using Cu radiation containing the following angle 2 theta values: 14.1° and 15.0°, and at least one angle theta value selected from the group consisting of: 19.5°, 17.9°, 10.5°, 15.4°, 28.1°, 18.4°, 18.2°, and 13.6°.

4. The crystalline hydrate mono hydrochloride salt of Compound I of claim 1 characterized by the X-ray powder diffraction pattern of FIG. 1.

5. The crystalline hydrate mono hydrochloride salt of Compound I of claim 1 having an x-ray powder diffraction pattern obtained using Cu radiation characterized by a reflection at a d-spacing of about 5.0 angstroms.

6. The crystalline mono hydrochloride salt of Compound I of claim 1 having an x-ray powder diffraction pattern obtained using Cu radiation characterized by a reflection at a d-spacing of about 5.0 angstroms, and at least one additional reflection at a d-spacing determined by X-ray powder diffraction using Cu radiation of about 6.3, 5.9, 4.6, 10.0, 5.8, 3.4, 8.4, and 4.3 angstroms.

7. The crystalline mono hydrochloride salt of Compound I of claim 1 having an x-ray powder diffraction pattern obtained using Cu radiation characterized by reflections at a d-spacing of about 6.3, 5.9, and 4.6 angstroms.

8. The crystalline monohydrochloride salt of Compound I of claim 7 further comprising an x-ray powder diffraction pattern obtained using Cu radiation characterized by reflections at a d-spacing of about 10.0, 5.8, and 3.4 angstroms.

9. The crystalline monohydrochloride salt of Compound I of claim 8 further comprising an x-ray powder diffraction pattern obtained using Cu radiation characterized by reflections at a d-spacing of about 8.4, 5.0, and 4.3 angstroms.

10. The crystalline hydrate mono hydrochloride salt of Compound I of claim 1 having a differential scanning calorimetry (DSC) peak melting temperature of about 221° C.

11. A pharmaceutical composition comprising a therapeutically or prophylactically effective amount of the crystalline hydrate mono hydrochloride salt of Compound I of claim 1, and a pharmaceutically acceptable carrier.

* * * * *